United States Patent
Massie et al.

(10) Patent No.: US 8,126,112 B2
(45) Date of Patent: Feb. 28, 2012

(54) OSSEO CLASSIFICATION SYSTEM AND METHOD

(76) Inventors: Ronald E. Massie, Lake Ozark, MO (US); Christopher J. Leslie, Lake Ozark, MO (US)

( * ) Notice: Subject to any disclaimer, the term of this patent is extended or adjusted under 35 U.S.C. 154(b) by 433 days.

(21) Appl. No.: 12/250,423

(22) Filed: Oct. 13, 2008

(65) Prior Publication Data

US 2009/0124882 A1 May 14, 2009

Related U.S. Application Data

(63) Continuation-in-part of application No. 11/932,809, filed on Oct. 31, 2007, which is a continuation-in-part of application No. 11/224,472, filed on Sep. 12, 2005, which is a continuation of application No. 10/351,567, filed on Jan. 24, 2003, now Pat. No. 6,944,262, which is a continuation-in-part of application No. 10/134,153, filed on Apr. 27, 2002, now abandoned, which is a continuation of application No. 09/452,348, filed on Dec. 1, 1999, now Pat. No. 6,381,301.

(51) Int. Cl.
*G01B 15/00* (2006.01)
(52) U.S. Cl. .......................................... 378/54; 378/38
(58) Field of Classification Search ............... 378/38–40, 378/54–56, 62
See application file for complete search history.

(56) References Cited

U.S. PATENT DOCUMENTS

| | | | |
|---|---|---|---|
| 3,949,229 A | 4/1976 | Albert | |
| 4,104,532 A | 8/1978 | Weiss | |
| 4,188,537 A | 2/1980 | Franke | |
| 4,239,971 A | 12/1980 | Cushman | |
| 4,259,853 A | 4/1981 | Fleissner | |
| 4,628,356 A | 12/1986 | Spillman | |
| 4,783,793 A | 11/1988 | Virta et al. | |

(Continued)

FOREIGN PATENT DOCUMENTS

CA 2390334 11/2008

(Continued)

OTHER PUBLICATIONS

"Notice of Reason for Rejection", Japan Patent Application No. 2006-502953 based on PCT/US2004/001825, (Aug. 3, 2009).

(Continued)

*Primary Examiner* — Hoon Song
(74) *Attorney, Agent, or Firm* — Law Office of Mark Brown, LLC; Mark E. Brown

(57) ABSTRACT

An osseo classification and digital modality modeling system includes a computer with a digital memory adapted for storing patient densitometry information, an input and an output. An input subsystem includes a pair of source/receptor units mounted on a signal positioning subsystem, which is adapted for moving the source/receptor units through predetermined paths of movement, which can be circular or linear. The resulting tomographic data is synthesized to form any 3-D model or image, which is output for further analysis and classifying osseo structure and/or prosthetic osseointegration. An osseo classification and digital tomosynthesis method includes the steps of moving a pair of sensor/receptor units relative to a patient. The resulting signals output by the receptor are digitized and synthesized to form a 3-D image or model. Multiple depths of penetration and multiple widths can be captured from single acquisitions using digital tomosynthesis signal processing techniques. Osseo structure and/or prosthetic osseointegration is classified using the densitometry data.

1 Claim, 19 Drawing Sheets

U.S. PATENT DOCUMENTS

| | | | |
|---|---|---|---|
| 4,813,060 A | 3/1989 | Heubeck et al. | |
| 4,823,369 A | 4/1989 | Guenther et al. | |
| 4,856,038 A | 8/1989 | Guenther et al. | |
| 4,941,164 A | 7/1990 | Schuller et al. | |
| 4,985,907 A * | 1/1991 | Moteni | 378/39 |
| 5,093,852 A | 3/1992 | Nishikawa et al. | |
| 5,195,114 A | 3/1993 | Sairenji et al. | |
| 5,214,686 A | 5/1993 | Webber | |
| 5,306,306 A | 4/1994 | Bisek et al. | |
| 5,335,260 A | 8/1994 | Arnold | |
| 5,480,439 A | 1/1996 | Bisek et al. | |
| 5,503,559 A | 4/1996 | Vari | |
| 5,528,645 A | 6/1996 | Koivisto | |
| 5,533,080 A | 7/1996 | Pelc | |
| 5,579,361 A | 11/1996 | Augais et al. | |
| RE35,423 E | 1/1997 | Adams et al. | |
| 5,677,940 A | 10/1997 | Suzuki et al. | |
| 5,784,429 A | 7/1998 | Arai | |
| 5,785,041 A | 7/1998 | Weinstein et al. | |
| 5,793,837 A | 8/1998 | Mezhinsky et al. | |
| 5,828,720 A | 10/1998 | Syrjanen | |
| 5,828,721 A | 10/1998 | Schulze-Ganzlin et al. | |
| 5,828,722 A | 10/1998 | Ploetz et al. | |
| 5,835,555 A | 11/1998 | Barry et al. | |
| 5,836,876 A | 11/1998 | Dimarogonas | |
| 5,838,765 A | 11/1998 | Gershman | |
| RE36,162 E | 3/1999 | Bisek et al. | |
| 5,917,882 A | 6/1999 | Khutoryansky et al. | |
| 5,917,883 A | 6/1999 | Khutoryansky et al. | |
| 5,930,327 A | 7/1999 | Lin | |
| 5,995,583 A | 11/1999 | Schick et al. | |
| 6,038,287 A | 3/2000 | Miles | |
| 6,069,935 A | 5/2000 | Schick et al. | |
| 6,320,931 B1 * | 11/2001 | Arnold | 378/56 |
| 6,381,301 B1 | 4/2002 | Massie | |
| 6,385,283 B1 | 5/2002 | Stein et al. | |
| 6,405,071 B1 | 6/2002 | Analoui | |
| 6,424,694 B1 | 7/2002 | Molteni | |
| 6,496,558 B2 | 12/2002 | Graumann | |
| 6,664,986 B1 | 12/2003 | Kopelman et al. | |
| 6,690,761 B2 | 2/2004 | Lang et al. | |
| 6,821,116 B2 | 11/2004 | Severance | |
| 7,099,428 B2 | 8/2006 | Clinthorne et al. | |
| 7,203,273 B2 | 4/2007 | Linnosaari | |
| 2002/0114425 A1 | 8/2002 | Lang et al. | |
| 2002/0178032 A1 | 11/2002 | Benn et al. | |
| 2005/0226374 A1 * | 10/2005 | Lang et al. | 378/54 |
| 2006/0067464 A1 * | 3/2006 | Clinthorne et al. | 378/38 |
| 2007/0133739 A1 * | 6/2007 | Hangartner et al. | 378/54 |

FOREIGN PATENT DOCUMENTS

| | | |
|---|---|---|
| EP | 0180482 | 5/1986 |
| EP | 0314506 | 5/1989 |
| EP | 0652433 | 5/1995 |
| EP | 1237483 | 11/2008 |
| WO | WO9311707 | 6/1993 |
| WO | WO-0138824 | 5/2001 |
| WO | WO 01/39667 | 6/2001 |

OTHER PUBLICATIONS

"Final Decision for Rejection", Japan Patent Application No. 2006-502953 based on PCT/US2004/001825.

"Notice of Reason for Rejection", Japan Patent Application No. 2001-541403 based on PCT/US00/32905, (Nov. 24, 2009).

Krennmair, Gerald, MD et al., "Maxillary Sinus Aspergillosis: Diagnosis and Differentiation of Sinus Concretions", American Association of Oral and Maxillofacial Surgeons,(1995),657-663.

"Notice of Reason for Rejection", Japan Appl. No. 2001-541403 corresponding to PCT/US00/32905.

Elsasser, Urs, P., et al., "Bone Density Measurement with Computed Tomography", *British Medical Bulletin* vol. 36, No. 3, (1980),293-296.

Exner, G., M., et al., "Bone Densitometry Using Computed Tomography", *British Journal of Radiology*, vol. 52, (1979),14-23.

Boyde, A. et al., "The Mineralization Density of Iliac Crest Bone From Children with Osteogenesis Imperfecta", A. Boyde, P. Travers, F.H. Glorieux, S. J. Jones, The Mineralization Density of Iliac Crest Bone From Children with Osteogensis Imperfecta, *Calcified Tissue International*, vol. 64 Issue 3, p. 185-190, (Mar. 1999), 185-90.

Branemark, M.D., Ph.D., Ingvar et al., "Tissue-Integrated Prosthese, Osseointegration in clinical denistry", *Quintassence Publishing Co., Inc.*, 1985, 11-70.

"International Search Report", PCT/US00/32905, (Jan. 26, 2001).

"Written Opinion of the ISA", PCT/US/04/01825, Feb. 25, 2005.

"Supplemental European Search Report", Massie Application No. 04704878.0, PCT/US2004001825, Jun. 10, 2008.

* cited by examiner

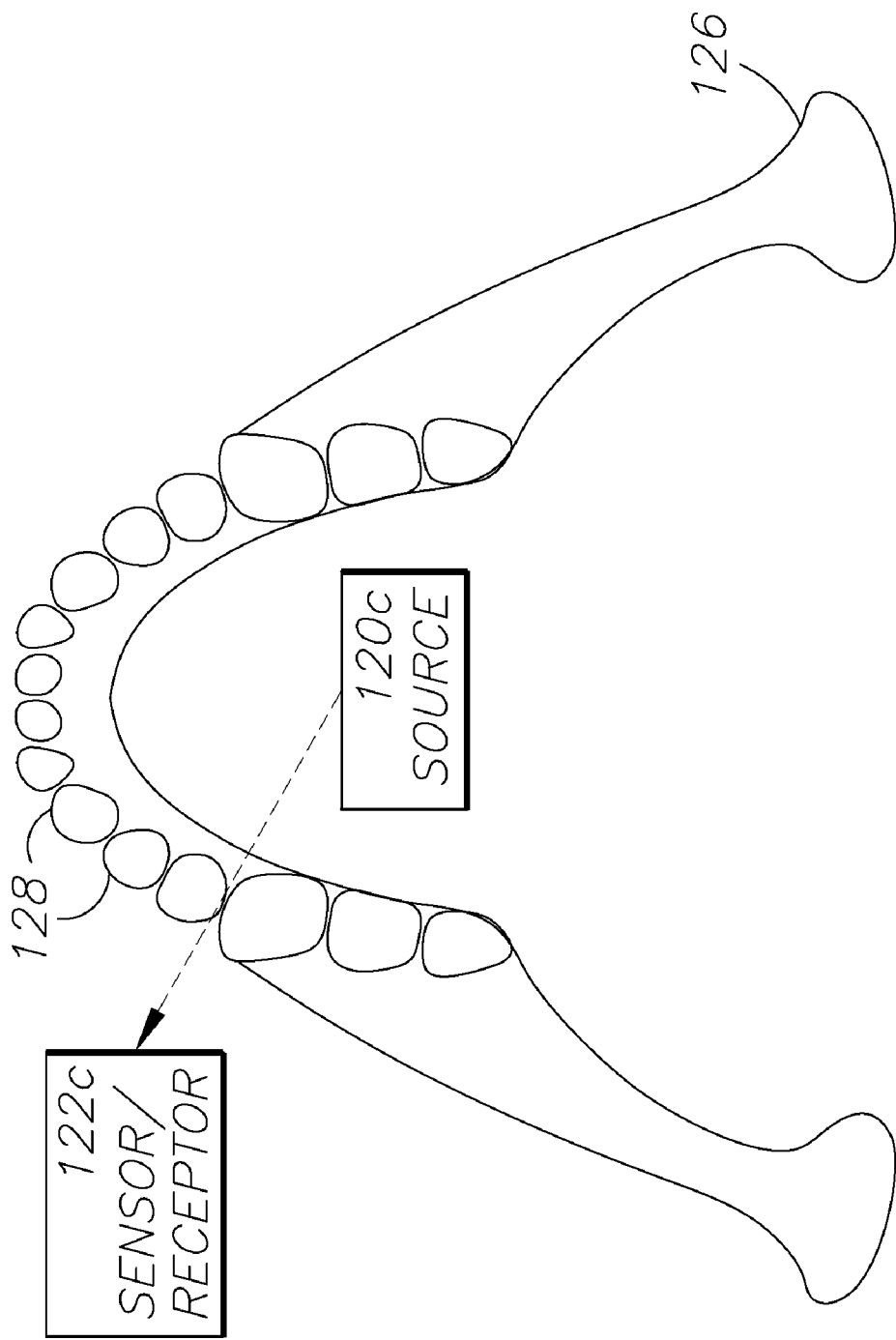

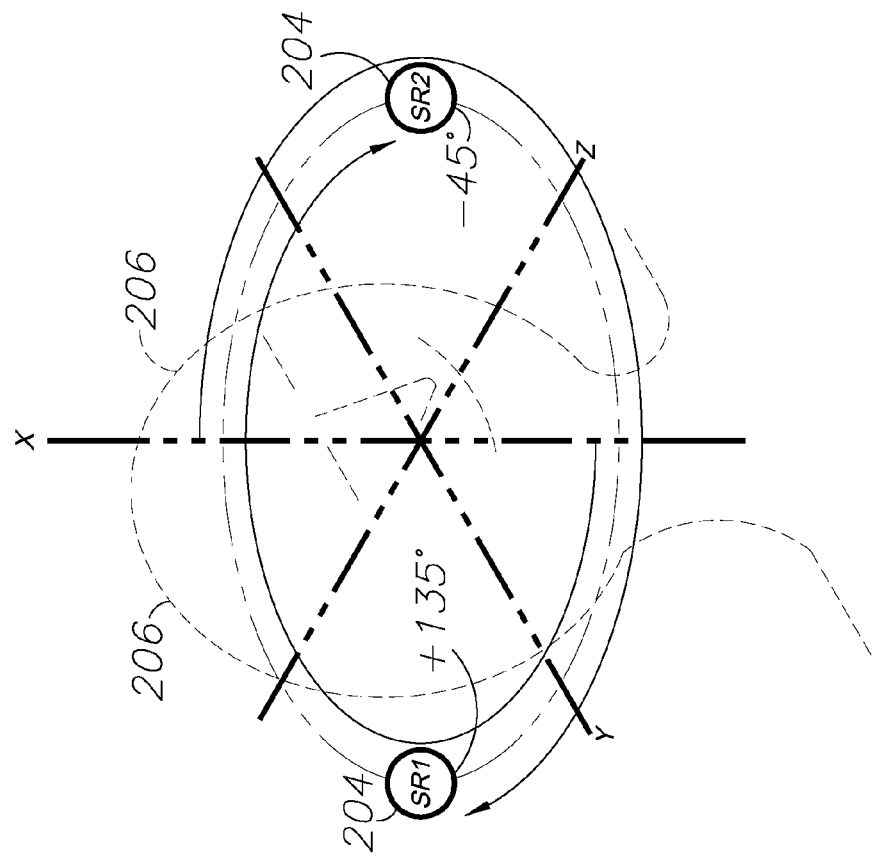
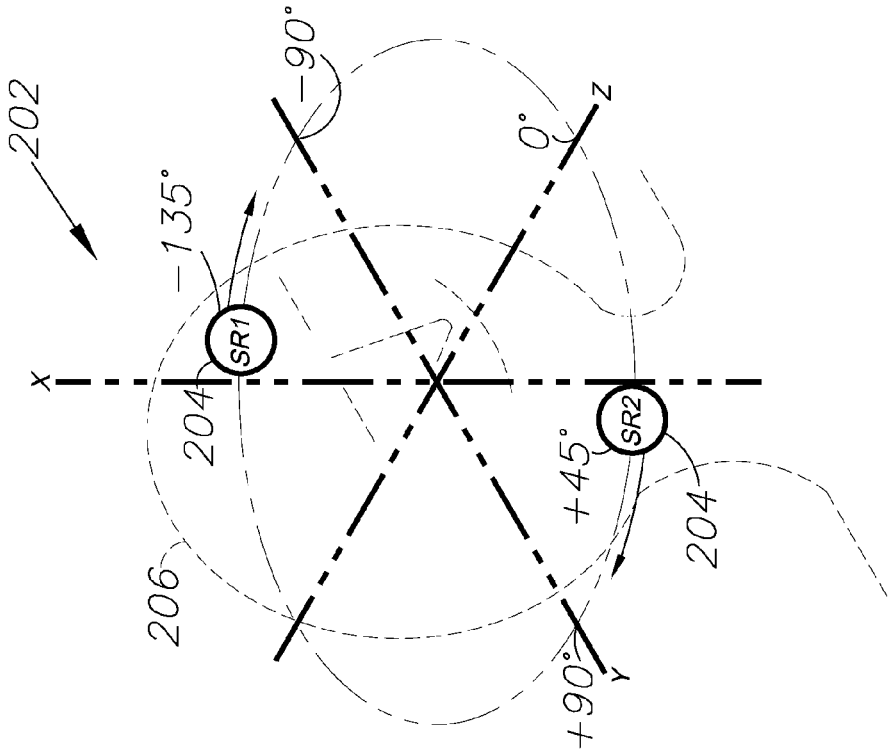
FIG. 8A
FIG. 8B

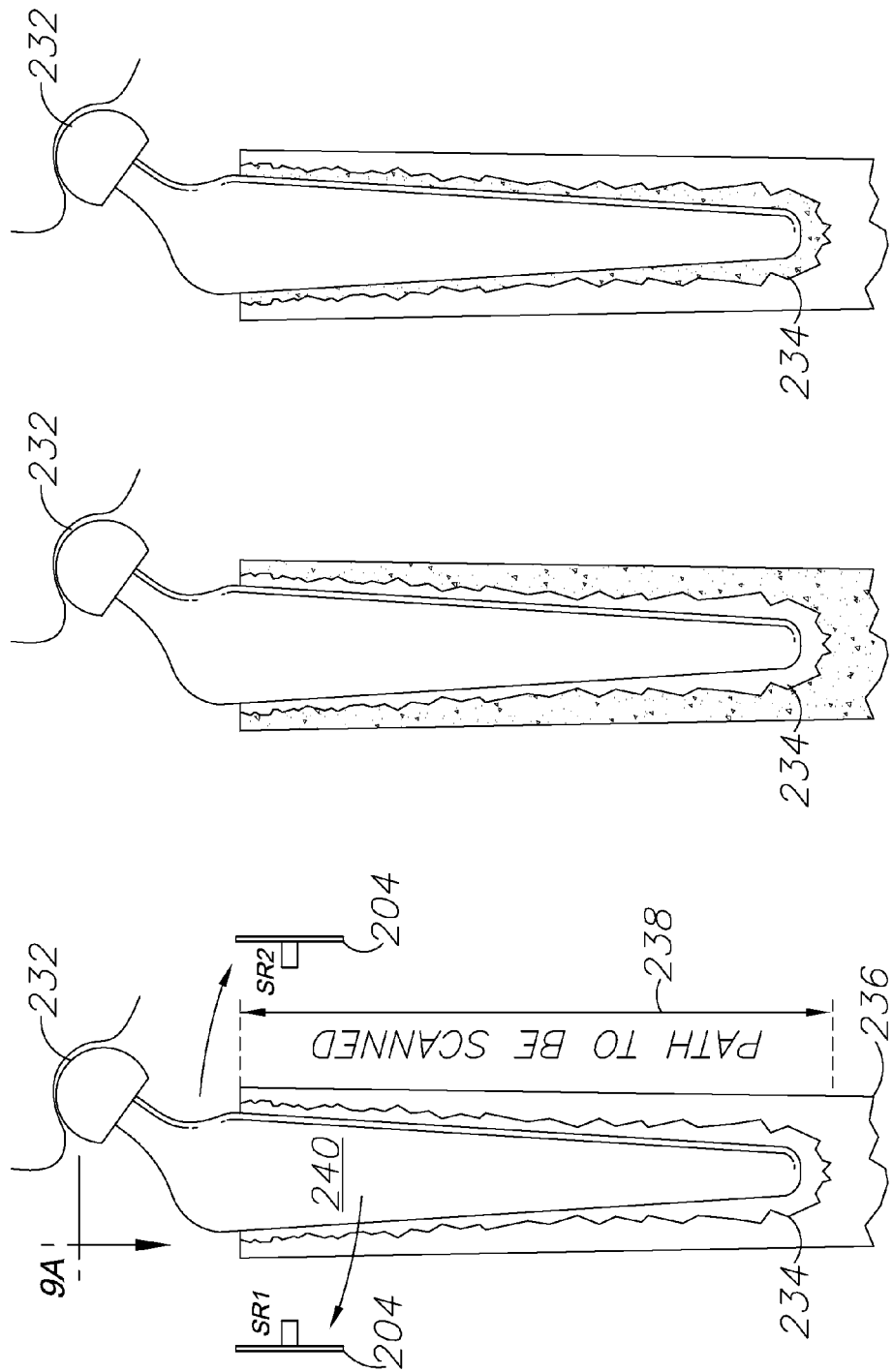

OSSEO CLASSIFICATION SYSTEM AND METHOD

CROSS-REFERENCE TO RELATED APPLICATIONS

This application is a continuation-in-part of Ser. No. 11/932,809 filed Oct. 31, 2007, which is a continuation-in-part of Ser. No. 11/224,472 filed Sep. 12, 2005, which is a continuation of Ser. No. 10/351,567, filed Jan. 24, 2003, now U.S. Pat. No. 6,944,262, which is a continuation-in-part of Ser. No. 10/134,153, filed Apr. 27, 2002, now abandoned, which is a continuation of Ser. No. 09/452,348, filed Dec. 1, 1999, now U.S. Pat. No. 6,381,301, in which priority is claimed and which are incorporated herein by reference.

BACKGROUND OF THE INVENTION

1. Field of the Invention

The present invention relates generally to digital modality modeling, such as tomosynthesis, and in particular to classifying bone types prior to dental and orthopedic procedures.

2. Description of the Related Art

The field of dental diagnostics is generally concerned with locating pathologies in the dental structure, i.e. the teeth and the surrounding tissue and bone. Some of the more common pathologies are: 1) caries associated with decay; 2) fractures; 3) apical abscesses; and 4) morphologies of pulpal chambers and canals. The system and method of the present invention are primarily, but not exclusively, concerned with detecting these pathologies and with orthopedics.

Early detection of dental pathologies is very important in minimizing damage. Conventional diagnosis procedures are generally performed using dental X-rays (both fixed beam and scanning beam), explorers, and other conventional equipment.

Incipient caries, particularly those located within the enamel surface, often go undetected with conventional equipment. When such caries are finally found, considerable damage to tooth structure may have already occurred. Subsurface, incipient caries are located entirely within the enamel layer of the teeth. They are particularly difficult to locate using conventional diagnostic equipment and procedures. By the time such incipient caries are located, the extent of the damage is often 17% to 23% greater than it would appear to be on a conventional X-ray negative.

Dental fractures can result from bruxism (teeth grinding), trauma, etc. The dental structure that has been weakened by various causes, such as decalcification, is particularly susceptible to fractures. Fractures can assume various configurations, including "craze", vertical, oblique and horizontal line patterns. Fracture patterns and configurations can be particularly difficult to locate using conventional X-ray equipment and procedures. For example, fractures which are generally parallel to the X-ray beam are often undetectable on an X-ray negative. Undetected, and hence untreated, fractures can provide direct paths through the enamel layer of the teeth whereby bacteria can invade the dentin and pulp layers. Pathologies in the dentin and pulp layers are often associated with considerable pain and tooth loss.

Apical abscesses comprise yet another dental condition which can be difficult to diagnose with conventional equipment, particularly in the early stages. Advanced apical abscesses can cause considerable pain because they involve the neurovascular bundles located in the root canals as well as the osseous tissue around the apex of the root. Early detection of apical abscesses can lead to appropriate, early-stage treatment, thus avoiding advanced disease processes with resultant pain, swelling, and other serious health consequences and complications.

Tomography or sectional radiography techniques using scanning X-ray beams have previously been employed for dental applications. For example, U.S. Pat. Nos. 4,188,537; 4,259,583; 4,823,369; 4,856,038; and 5,214,686 all relate to dental X-ray diagnosis utilizing scanning techniques and are incorporated herein by reference.

In the medical field, densitometry procedures are used for measuring bone morphology density (BMD) by utilizing scanning X-ray beam techniques. Examples are shown in U.S. Pat. Nos. 5,533,080; 5,838,765; and Re. 36,162, which are incorporated herein by reference. Medical applications of densitometry include the diagnosis and treatment of such bone diseases as osteoporosis. Dual energy x-ray absorptiometry (DEXA) utilizes x-rays with different peak energy levels for distinguishing soft and hard (e.g., muscle and skeletal) tissue structures based on their absorption of the x-rays at different energy levels.

The availability of relatively fast computers with large memories at reasonable costs has led to the digitalization of X-ray images for mapping BMD models in various formats. For example, BMD images use color to identify varying densities. Digital BMD patient models are also used for comparison purposes with standard models and with patients' own prior BMD histories. Age correction factors can be applied to patients' models for diagnosing and monitoring the onset and progress of such medical conditions as osteoporosis and the like. The present invention utilizes such densitometry modeling and mapping techniques for dental applications.

In addition to pathology detection and diagnosis, the present invention has applications in monitoring osseointegration, which occurs at the interface between bone structures and prostheses, such as implants and replacement joints. For example, dental implants osseointegrate with patients' dental structure. The application of tomographical densitometry techniques to osseointegration monitoring can provide the dental or medical practitioner with important information in evaluating the effectiveness of implant procedures.

Digital tomosynthesis utilizes computers for digitizing tomographic densitometry data and constructing 3-D models of patient and prosthetic regions of interest (ROIs). Using digital tomosynthesis techniques, partial rotation of source/receptor units and relatively few discrete exposures can produce sufficient information to construct 3-D models. By digitally processing the resulting images, tomographic slices at different depths and with different thicknesses can be reconstructed from individual data acquisitions, thus minimizing radiation exposure and procedure time. Digital tomosynthesis techniques have been utilized in mammography applications. The resulting 3-D digital tomosynthesis models are utilized for diagnostic, treatment, forensic and related purposes.

Other modeling and imaging modalities include computerized tomography (CT), magnetic resonance imaging (MRI), ultrasound, sonar, Doppler effect, photon emission tomography (PET) and single photon emission computed tomography (SPECT) scanning. The present invention is adapted for medical and dental applications involving the acquisition of signals, which are digitized and further processed to produce 3-D models corresponding to patient regions of interest (ROIs) including both hard and soft tissue structures and prosthetics.

Implants and other prostheses are used extensively in connection with treating a wide variety of dental and orthopedic conditions. The success of such implants commonly depends on the osseointegration of the implants, i.e. the extent of direct, structural and functional connection between ordered living bone and the surface of the implant. Osseo integration is directly related to endogenous factors such has bone quality and quantity. Radiographic diagnosis and resistance to cutting and drilling are generally accepted as the criteria for classifying bone quality as follows:

Type 1 comprising substantially entirely homogenous compact bone;

Type 2 comprising a thick layer of compact bone surrounding core of dense bone;

Type 3 comprising a thin layer of cortical bone surrounding a core of tents trabecular bone; and Type 4 comprising a thin layer of cortical bone surrounding a core of low density, weak trabecular bone.

Classifying bone types has involved a wide variety of imaging procedures, such as radiography, computerized tomography (CT), magnetic resonance imaging (MRI) and ultrasound. Each has certain advantages and disadvantages. Dual energy x-ray absorptiometry (DEXA) is widely used, particularly for determining bone mass density (BMD) for diagnosing osteoporosis and other conditions, and for assessing fracture risks. Bone density normally varies with such factors as age and gender. DEXA test results are commonly reported as a combination of: measured density ($g/cm^3$); Z-score (standard deviations above or below the mean for the patient's age and gender); and T-score (standard deviations above or below the mean for a healthy 30-year-old adult of the same gender). Based on such information, susceptibility to fracturing and prosthesis osseo-integration can be predicted. However, additional information and analysis would be useful to the health-care practitioner, particularly in connection with prosthetic implant procedures.

Heretofore there has not been available a system or method for applying digital tomosynthesis and related modalities for classifying bone densities, e.g., prior to dental and orthopedic procedures, with the advantages and features of the present invention.

SUMMARY OF THE INVENTION

In the practice of an aspect of the present invention, a digital tomosynthesis, or related modality, system and method are provided for dental and orthopedic densitometry modeling. The system utilizes a controller (computer) with a microprocessor and a digital memory device. An input device inputs data to the microprocessor for controlling the operation of the modeling system and for providing a database including densitometry parameters for comparison with a patient's densitometry model. The controller controls the operation of X-ray equipment, which is adapted for scanning patients' dental and orthopedic structures along preprogrammed scan paths. The X-ray output is processed by the microprocessor for creating a densitometry model, which can be output in various formats. In the practice of the method of the present invention, a patient and the X-ray equipment are positioned relative to each other. A controller is preprogrammed with a scan path and with data corresponding to the patient. The X-ray equipment emits and detects X-ray beams at first and second energy levels to provide densitometry output. The densitometry output is digitized and merged to provide a tomographic model, which can be compared to predetermined parameters unique to the patient. The model can be output in various formats, including a visual image color-coded to depict varying dental and orthopedic structure densities. Applications of the system and methodology include diagnosis, treatment, identification, forensics and biometrics. Digital tomosynthesis techniques can also be utilized with the present invention, and include both dental and orthopedic applications. Combined source and receptor units can be rotated or moved axially around and along multiple axes to capture data for synthesizing by the computer, which provides output in the form of 3-D images and models.

Another application involves a method of classifying bone types prior to procedures, such as dental and medical prosthetic implants.

The drawings constitute a part of this specification and include exemplary embodiments of the present invention and illustrate various objects and features thereof.

BRIEF DESCRIPTION OF THE DRAWINGS

FIG. 4C is a diagram of an application with an internal beam source and an external sensor/receptor.

FIGS. 8A-D show an alternative embodiment of the invention comprising a pair of sensor/source units adapted for rotating around a patient in multiple planes defined by X, Y and Z axes.

FIG. 10 shows an application of the invention in connection with a hip prostheses.

FIG. 11 shows an application of the invention in connection with the hip prostheses, with a filtering technique for particularly displaying bone material.

FIG. 12 shows an application of the invention in connection with the hip prosthesis, with a filtering technique for particularly displaying an interface between the bone and the prosthesis.

DETAILED DESCRIPTION OF THE PREFERRED EMBODIMENTS

I. Introduction and Environment

Figure 1:
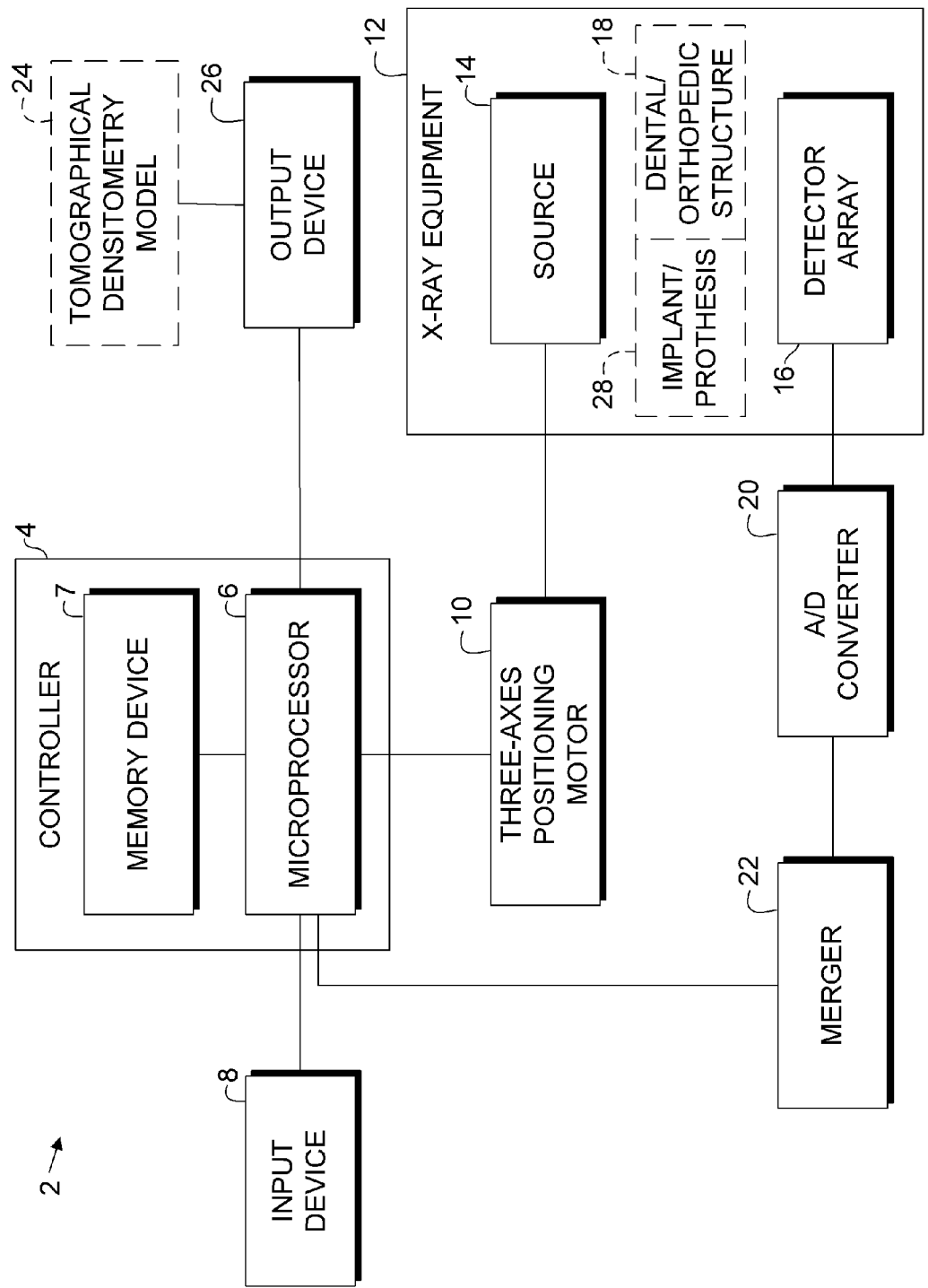
FIG. 1 is a schematic, block diagram of a dental and orthopedic densitometry modeling system embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. "Modeling" is used broadly herein to cover capturing, converting, creating, analyzing and storing patient information, such as densitometry, using various modalities for a variety of applications such as imaging, diagnostics, forensics, etc. Examples discussed herein are not to be interpreted as limiting.

II. Dental Densitometry Modeling System 2

Referring to the drawings in more detail, the reference numeral 2 generally designates a dental and orthopedic densitometry modeling system embodying the present invention. The system 2 includes a controller 4 with a microprocessor 6 connected to a digital memory device 7. The hardware components of the controller 4, i.e. the microprocessor 6 and the memory device 7, can comprise any of a number of suitable hardware devices which are commercially available and are suitable for this application. In addition to various programmable logic devices (PLDs) and special-purpose microprocessors, general purpose, commercially available personal computers can be utilized in the controller 4. The controller 4 can be programmed in any suitable manner utilizing any of a variety of commercially available programming languages and software development systems.

The microprocessor 6 is adapted to receive input from one or more input devices 8, such as a keyboard, a pointing device (e.g., a mouse), a communications link, or another computer. Without limitation on the generality of useful data which can be input via the input device(s) 8, such data can include: 1) a patient's dental and orthopedic records, including previous tomographical densitometry models; 2) baseline tomographical densitometry models, which can be adjusted to accommodate for such factors as age, gender, size, weight, etc.; and 3) a preprogrammed scan path for the X-ray equipment.

The microprocessor 6 controls a positioning motor 10 which is operably connected to X-ray equipment 12 and is adapted for moving same through three axes of movement. Examples of X-ray equipment adaptable for use with the present invention are disclosed in U.S. Pat. Nos. 5,533,080; 5,838,765; and U.S. Pat. No. Re. 36,162, which are incorporated herein by reference. The X-ray equipment 12 includes an X-ray beam source 14 and a detector array 16. The X-ray beam can suitably collimated to assume any suitable configuration, such as fan, pencil, cone, etc. With the scanning technique disclosed, a restricted (i.e. collimated) beam is preferred. The source and the detector array 14, 16 are adapted for positioning on either side of a patient's dental/orthopedic structure 18.

Analog signals from the detector array 16 are output to an analog-to-digital (A/D) convertor 20, from which digitized signals are transmitted to a merger device 22 for merging into formats suitable for processing and analyzing by the microprocessor 6. The microprocessor 6, using data from the merger device 22, creates a tomographical densitometry model 24 which is transmitted to an output device or devices 26. Without limitation on the generality of useful output devices 26, it can comprise a monitor, a display, a printer, a communications link, and/or another computer. For example, a color printer can be utilized to provide a color-coded graphical representation of the tomographical densitometry model 24. The color coding can correspond to densities, thus identifying potential problem areas where decalcification has occurred and resulted in lower density. The tomographical densitometry model 24 can also be useful for monitoring osseointegration, since the density of the dental/orthopedic structure 18 (tissue and bone) in the vicinity of an implant 28 or other prostheses can provide an important diagnostic tool for the use of the dental or medical practitioner in assessing the effectiveness of an implant or prosthetic procedure. The tomographical densitometry model 24 is also entered into the computer's memory device 7.

III. Dental and Orthopedic Densitometry Modeling Method

Figure 2:
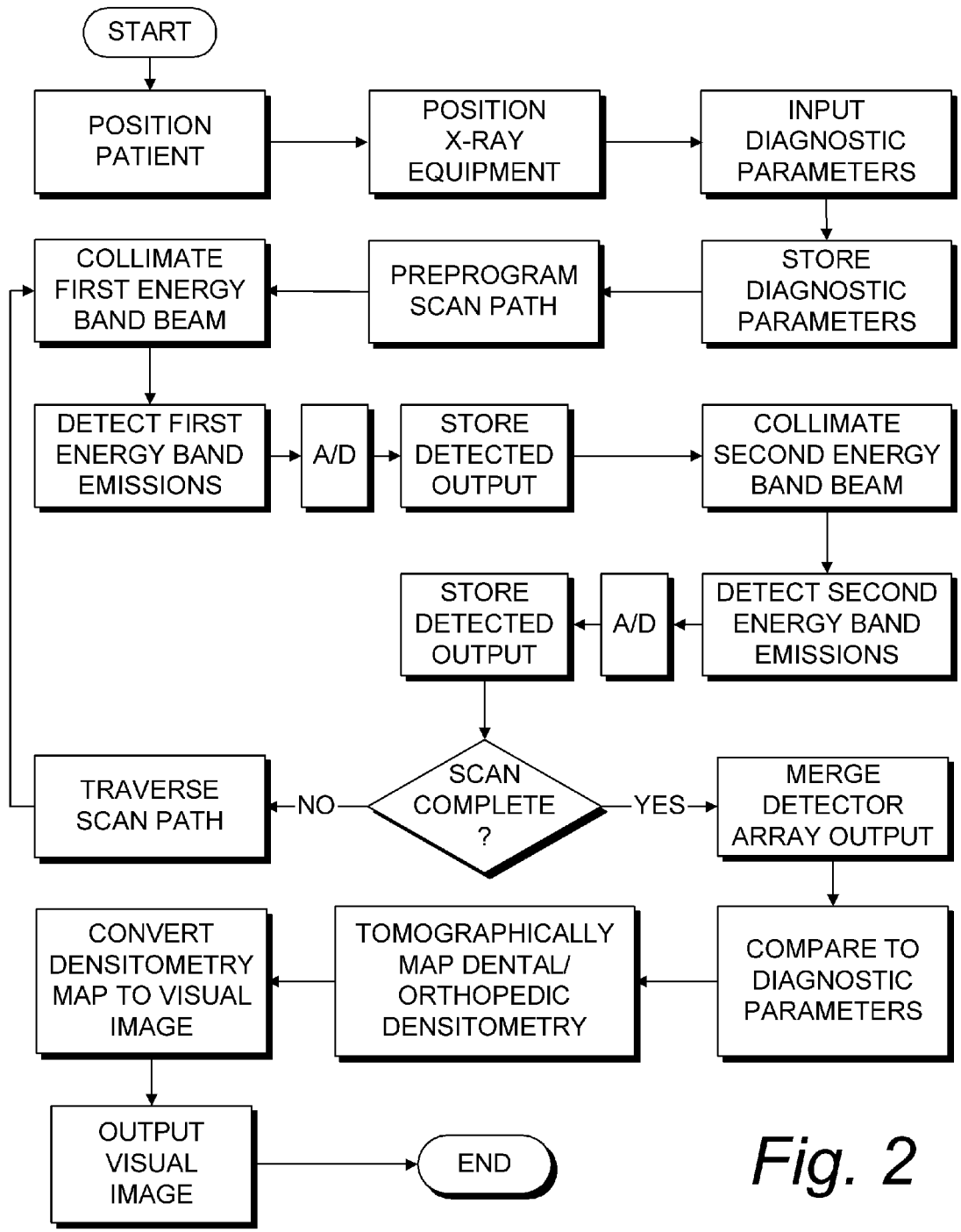
FIG. 2 is a flowchart of a dental and orthopedic densitometry modeling method embodying the present invention.

FIG. 2 is a flow chart of a dental and orthopedic densitometry method embodying the present invention. The method steps include positioning a patient and positioning the X-ray equipment relative to the patient, i.e. with the patient's dental/orthopedic structure to be examined located between the X-ray source 14 and the detector array 16.

Diagnostic parameters are input to the system and can comprise, for example, the patient's prior tomographical densitometry models and standardized models. The tomographical densitometry models can be corrected and/or adjusted to account for patients' age, gender, physical characteristics, etc. The input diagnostic parameters can be stored in the computer's memory device. A scan path for the X-ray equipment is preprogrammed in the computer.

The scanning procedure is commenced by collimating a first energy band beam, detecting emissions from same with a detector array, and converting the analog output of the detector array to a digital signal. The digital signal is output for storage in the computer. The steps of collimating the energy band beam and detecting, digitizing and storing same are repeated for a second energy band beam. The Bisek et al. U.S. Pat. No. Re. 36,362 discloses the use of dual-energy X-ray beams in medical densitometry applications. As discussed therein, dual-energy densitometry can result in a more accurate patient model.

The X-ray equipment then traverses the preprogrammed scan path and the first/second energy band steps are repeated until the scanning procedure is complete. The digitized detector array output is merged and compared to the diagnostic parameters which are stored in the computer's memory. The dental/orthopedic densitometry is tomographically modeled and output, for example to a monitor or printer for converting the model to a visual image. The visual image is output in a visible form for use by dental and medical practitioners.

IV. Modified Embodiment Densitometry Modeling Systems 102

Figure 3:
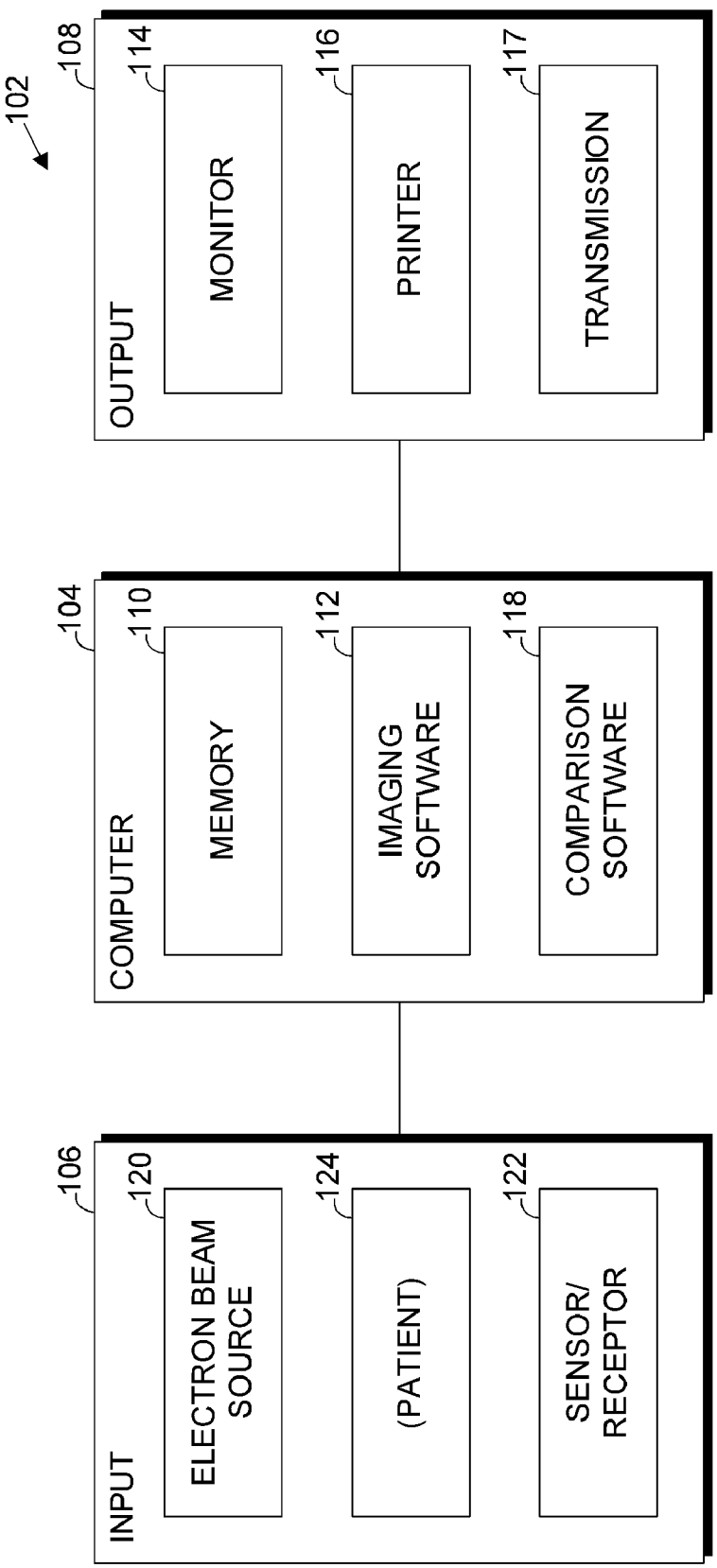
FIG. 3 is a block diagram of a dental or orthopedic densitometry modeling system comprising a first modified embodiment of the present invention.

A densitometry modeling system 102 comprising a first modified embodiment of present invention is shown in FIG. 3 and generally includes a computer 104 with an input 104a and an output 104*b*. Input and output devices 106 and 108 are connected to the computer input and output 104*a,b* respectively.

The computer 104 includes a memory 110, such as a hard drive, a tape drive, an integrated circuit (e.g., RAM) or some other suitable digital memory component, which can be either internal or external to the computer 104. Imaging software 112 is provided for converting the digital data into images, which are adapted for visual inspection by displaying same on a monitor 114 or by printing same on a printer 116 of the output device 108. Such images can also be transmitted by a suitable transmission device 117, such as a fax or modem. The computer 104 also includes comparison software 118, which is adapted for digitally comparing baseline and patient-specific dental and orthopedic densitometry models.

The input device 106 includes a beam source 120 and a sensor/receptor 122, which are adapted for positioning with at least a portion of the patient 124 therebetween. A wide variety of source and sensor/receptor combinations are included in the scope of the present invention. Preferably the beam source 120 emits a collimated beam adapted for scanning the patient's dental/orthopedic structure. Such devices can be located internal or external to the patient and include "wands" and "pens". Micro devices are also available that are adapted for mounting on the end of a stylus apparatus. Both hardwired and wireless (RF) types of source devices can be employed. External devices include beam heads mounted on articulated arm assemblies, which are commonly found in dental operatories and other medical workstations. Various hand-held, fixed-position and enclosure-type devices can also provide the beam emissions. Control of beam source 120 can be automated with the computer 104, or manual in the case of hand-held devices.

The sensor/receptor 122 can likewise be positioned internal or external to the patient. For example, various types of intraoral sensors are available. Phosphorus film sensors are used like X-ray film and are converted and "read" by the computer to transfer the digital data recorded thereon. Other types include charge coupled devices (CCD) and charged metal oxide semiconductor (CMOS) devices, which output digital data from respective circuits associated therewith. Micro printed circuits can be installed on such sensors and provide digital sensor output to the computer input 104*a*.

Still further, either or both of the beam source 120 and the sensor/receptor 122 can be preprogrammed for computer-controlled movement with respect to the patient 124. Thus, panoramic or tomographic images can be obtained with the patient immobilized. Such equipment is commercial available and typically moves through an arc of approximately 120 degrees for dental applications. The specific beam source 120 and sensor/receptor 122 components can be chosen as necessary for the type of model desired. For example, periapical, bite wing, full mouth, panoramic and cephalometric imaging are all widely used in dentistry, oral surgery and related fields. Still further, the system contemplates removable use on and inspection of individual tooth anatomy by use of a wand, pen or similar device adapted for placement intraorally by the dentist. Thus, the densitometry changes with respect to particular "watch" areas can be closely monitored.

Yet another type of beam source 120 comprises a miniaturized, hand-held CRT adapted for localized applications. For example, areas deemed susceptible to incipient caries and decay can be diagnosed and identified as "watch" areas, which the dental practitioner would specifically examine with such a miniaturized CRT source device during the course of follow-up office visits and procedures. Thus, patients would be exposed to only minimal levels of radiation in connection with such highly localized and tooth-specific densitometry models. An advantage of the system 102 is that models can be processed and compared nearly instantaneously. Thus, in a single appointment the dentist can obtain, compare and analyze multiple, limited-scope densitometry models specifically directed to areas of concern.

Figure 4A:
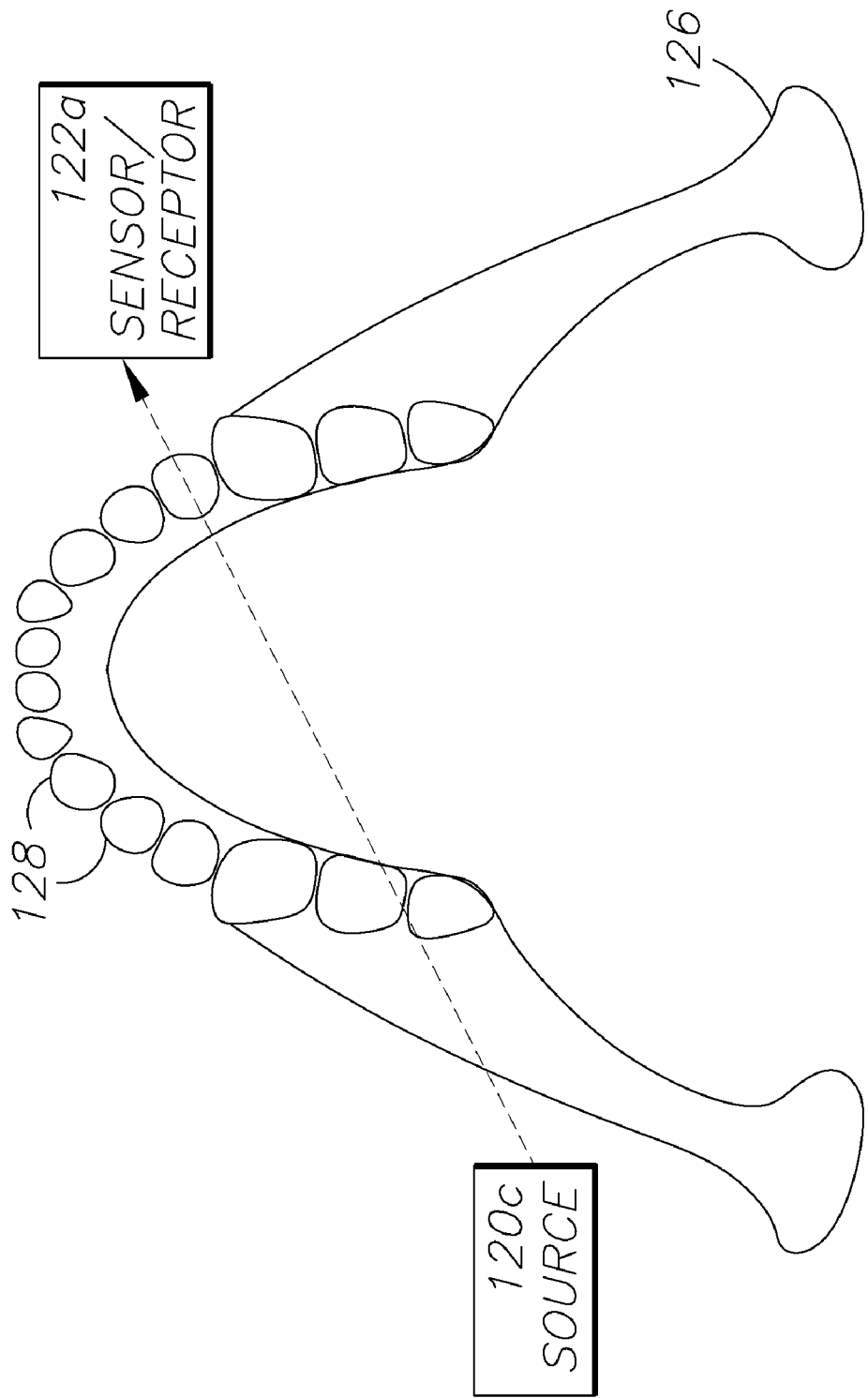
FIG. 4A is diagram of an application with an external beam source and an external sensor/receptor.
Figure 4B:
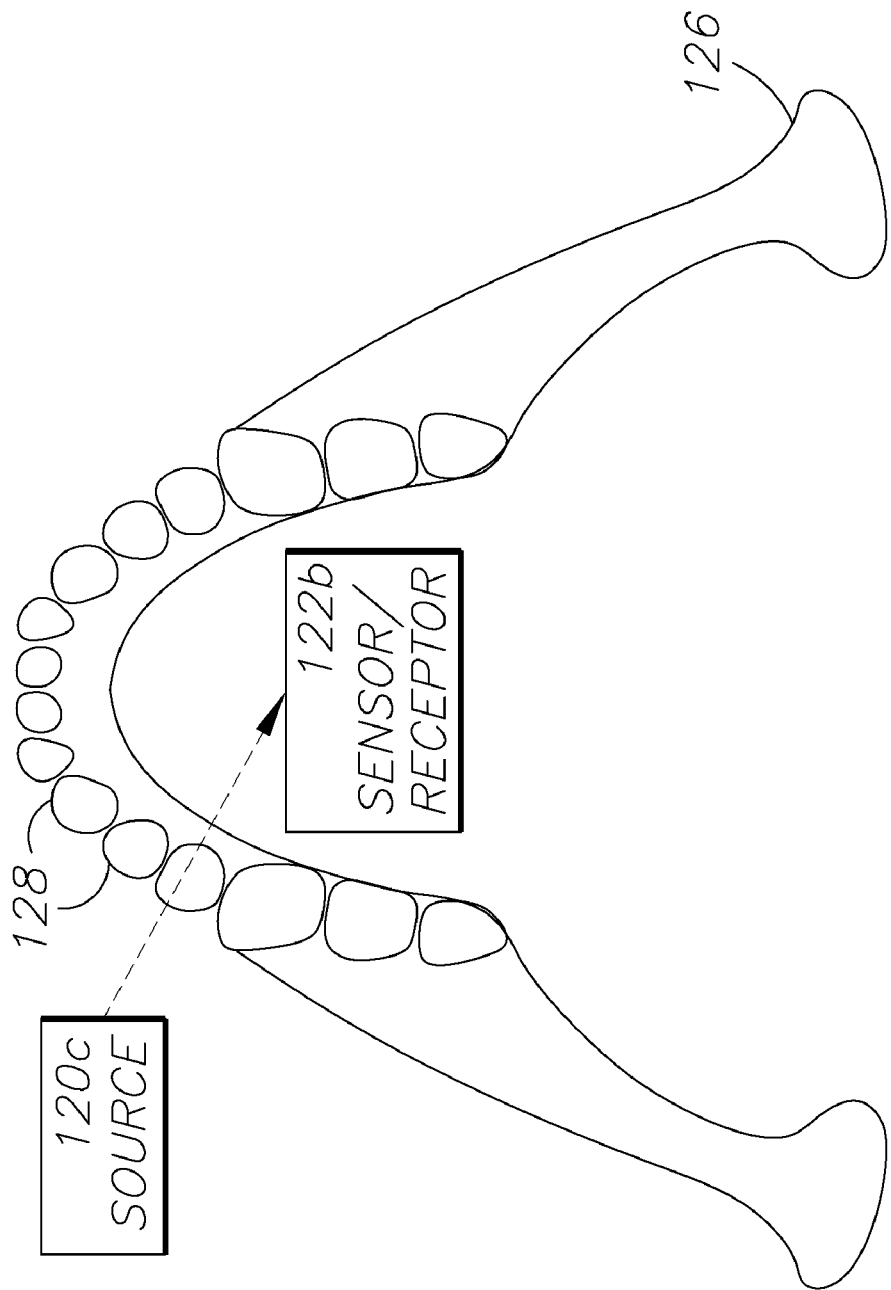
FIG. 4B is a diagram of an application with an external beam source and an internal sensor/receptor.
Figure 4D:
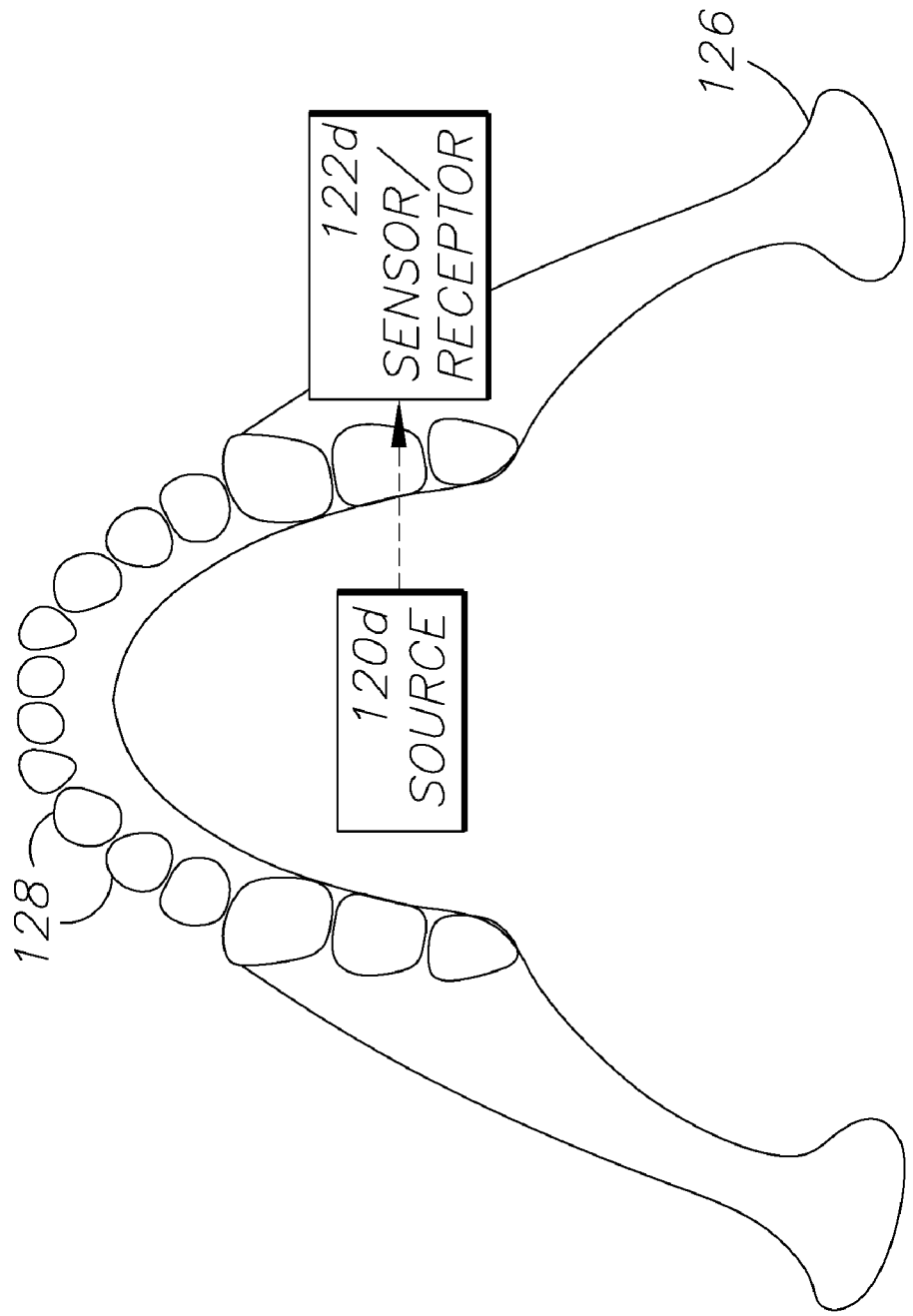
FIG. 4D is a diagram of an application with an internal beam source and an internal sensor/receptor.

FIGS. 4A-D show alternative configurations and placements of the beam sources 120 and the sensor/receptors 122 with respect to the mandible 126 and teeth 128 of the patient 124. FIG. 4A shows a beam source 120*a* and a sensor/receptor 122*a* both placed externally whereby the beam passes through the patient 124. Such configurations can be preprogrammed to travel through predetermined arcs or orbits around the patient 124 in order to compile a panoramic, whole mouth or cephalometric image. FIG. 4B shows an external beam source 120*b* and an internal sensor/receptor 122*b*. FIG. 4C shows an internal beam source 120*c* and an external sensor/receptor 122*c*. FIG. 4D shows both the beam source 120*d* and the sensor/receptor 122*d* positioned intraorally.

V. Modified Densitometry Modeling Methods and Applications

Figure 5:
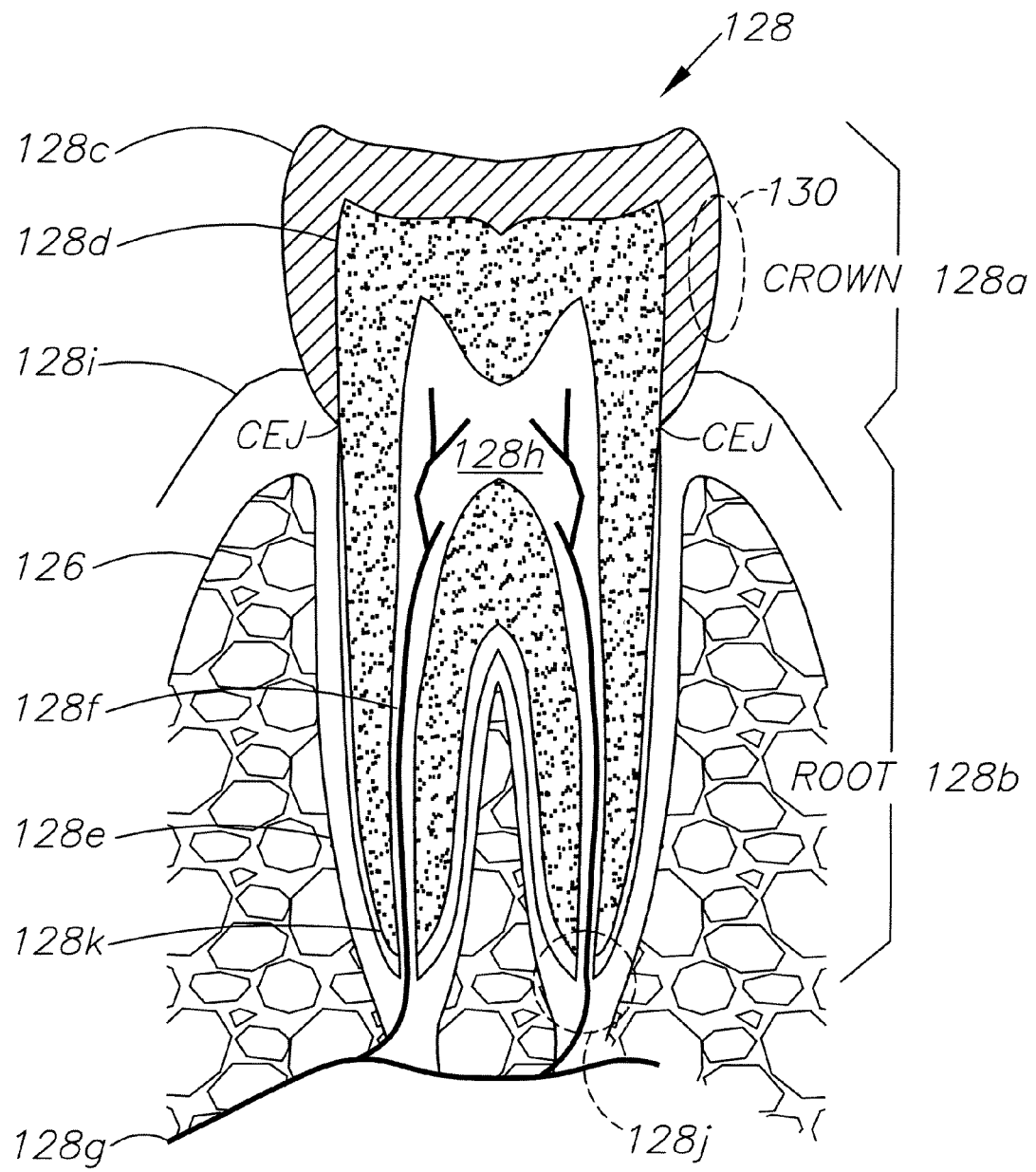
FIG. 5 is a diagram of a tooth structure, showing the locations of particular areas that are suited for densitometry monitoring with the system and method of the present invention.

Without limitation on the generality of useful dental and orthopedic applications of the modeling methods and applications for the present invention, several dental applications are described in detail. FIG. 5 shows a tooth 128 with a crown 128*a* and a root 128*b*. The crown 128*a* includes enamel 128*c* covering dentin 128*d*. The root 128*b* is embedded within a periodontal membrane 128*e* and includes a root canal 128*f* through which a neurovascular bundle 128*g* comprising a nerve, artery, vein and lymphatic components passes. The root canal 128*f* is filled with pulp 128*h* and surrounded by cementum 128*k*. The root 128*b* is embedded in the bone structure of the mandible or the maxilla 126, over which the gingiva and the gingival fibers 128*i* are located. The cementoenamel junction (CEJ) is located where the crown 128*a* meets the root 128*b* and is the common reference point for periodontal disease. Locations on the crown 128*a* between the adjacent teeth 130 are common locations for caries because bacteria tend to congregate in such locations unless dislodged by brushing and flossing. Another common problem area is located at the root apex 128*j*, where abscesses form.

Figure 6A:
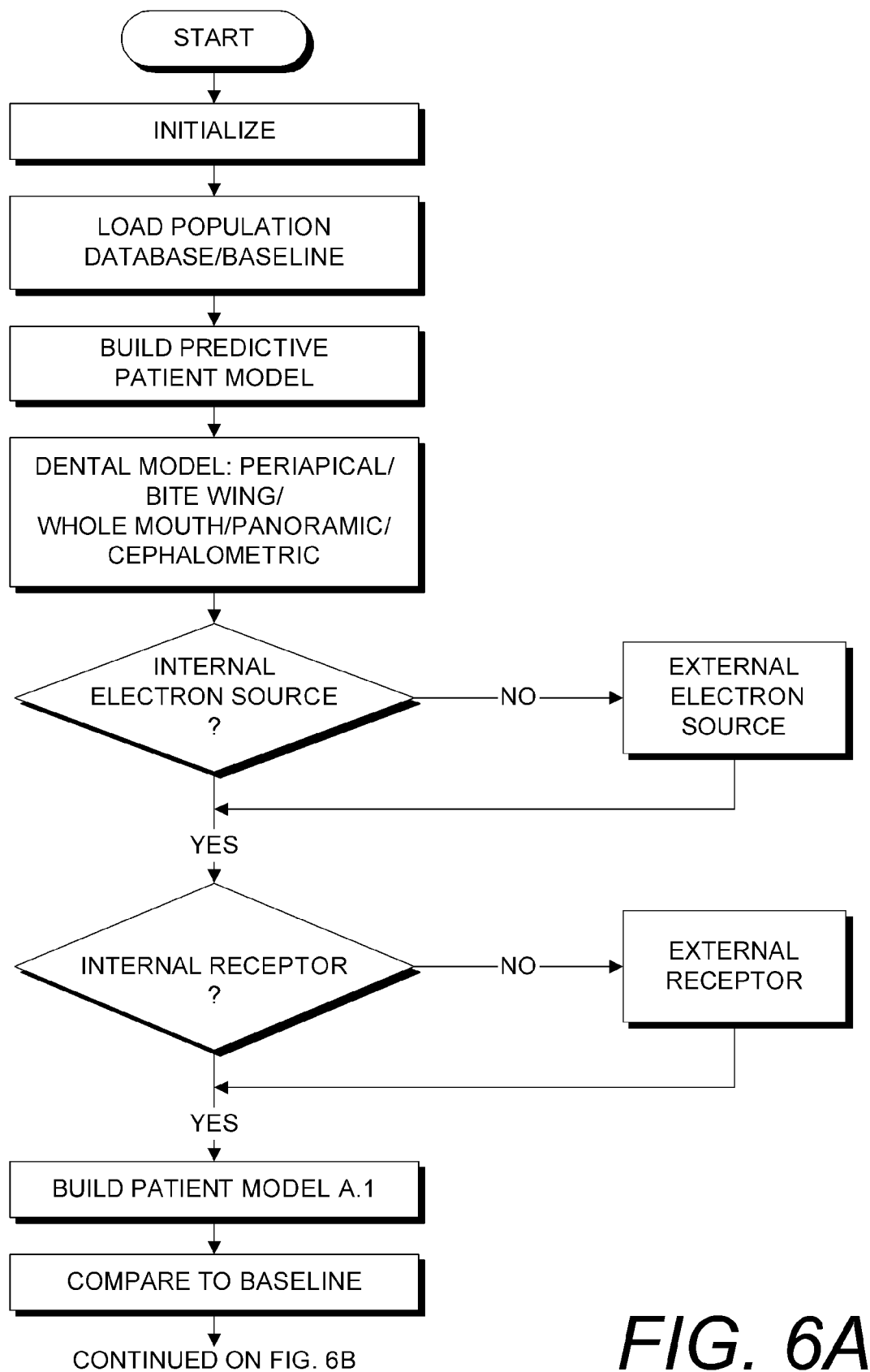
FIGS. 6A,B show a flowchart of a patient-specific densitometry modeling method according to the present invention.
Figure 6B:
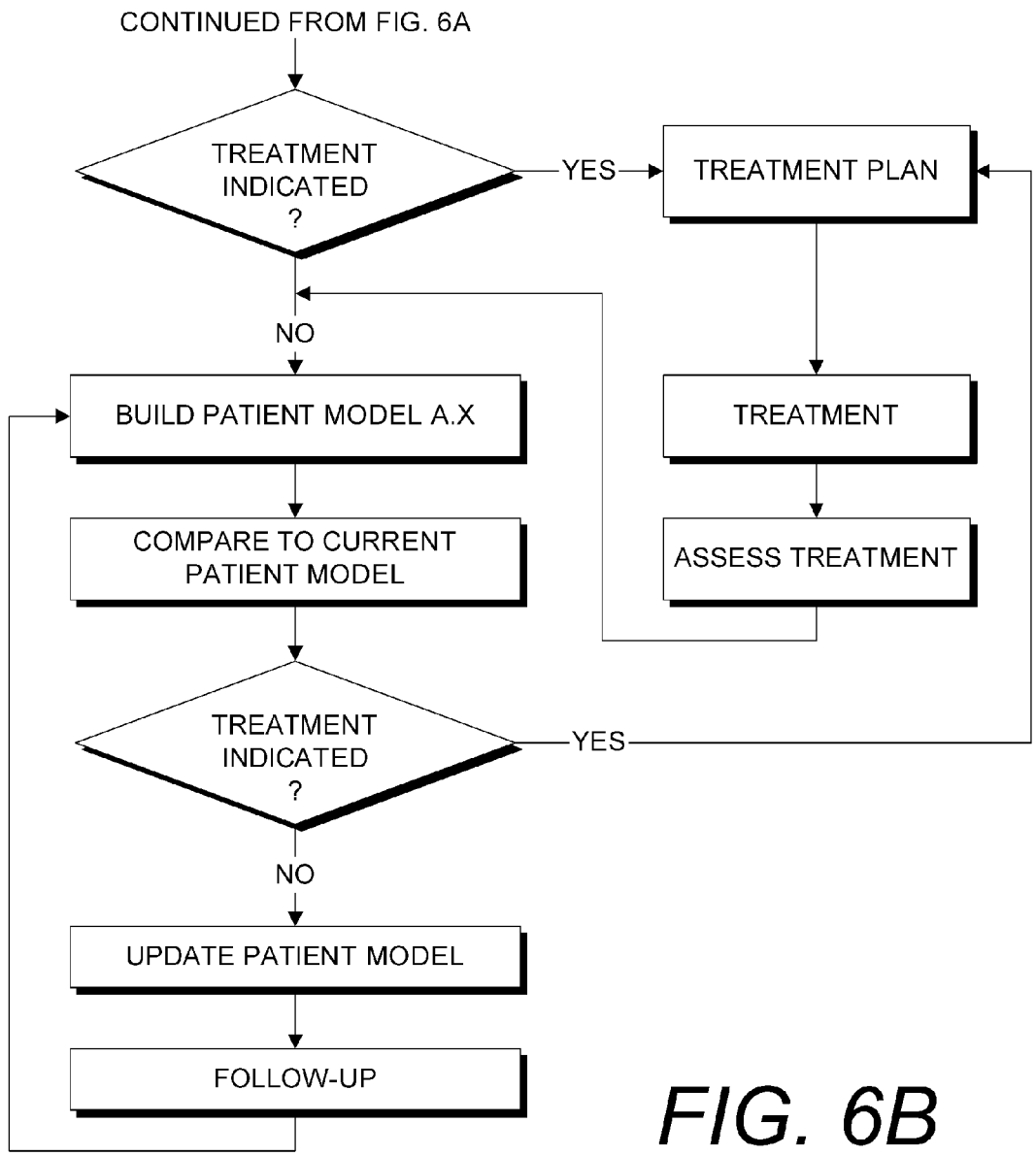

FIGS. 6A-B show a flowchart of the densitometry modeling method with respect to an individual patient. The steps of the flowchart generally correspond to routines, which can be performed either manually or with the computer 104. After starting and initializing the software, a population database/baseline is loaded. The population database/baseline can included densitometry data pertaining to the general population, or population subsets grouped by such variables and as age, gender, geographic area, etc. A predictive patient model is created from both population database information and patient-specific information, as discussed in more detail below. Examples of typical information used for creating dental models are shown, and include periapical, bite wing, whole mouth, panoramic and cephalometric densitometry data captures. Other types of data would be captured and used for creating patient models for other applications, such as orthopedic. Internal/external source/receptor selections (see FIGS. 4A-D) are made at the appropriate decision steps.

An initial patient model is created, and can be compared to a corresponding baseline model for "normal" dental/orthopedic densitometries in individuals of corresponding age, gender and other variables. The initial model can be designated A.1. If indicated, treatment can be performed.

In a follow-up session, a second model A.X can be built. The variable "X" can correspond to, for example, the version number or a time period, such as the number of days since the first model A.1 was created. The software can perform a comparison between the two patient-specific models A. 1 and A.X. Densitometry changes can be noted and brought to the attention of the dentist or physician. For example, areas showing significant decreases in densitometry would alert the dentist to the possibility of incipient caries. Depending on the extent of change and compromised density, preemptive treatment might be indicated, or the area can be designated for careful future monitoring for further deterioration or change. Because certain changes are normal, the baseline, plus the patient's dental/medical history, can be utilized in distinguishing conditions requiring treatment from normal decalcification/calcification.

Implant osseointegration can also be monitored with the system and methodology of the present invention. For example, the densitometry techniques described herein can monitor the progress of a bone-implant interface, indicating successful osseointegration, whereas the continued or increased presence of soft tissue granulation would indicate a failed implant.

Other conditions that are particularly well-suited for monitoring with the system and method of the present invention include fractures, decay, abscesses, plaque and periodontal disease. Still further, 3D imaging can be provided with the system and method whereby fractures and other lesions, which are difficult to detect in 2D imaging, can be made apparent.

Figure 7:
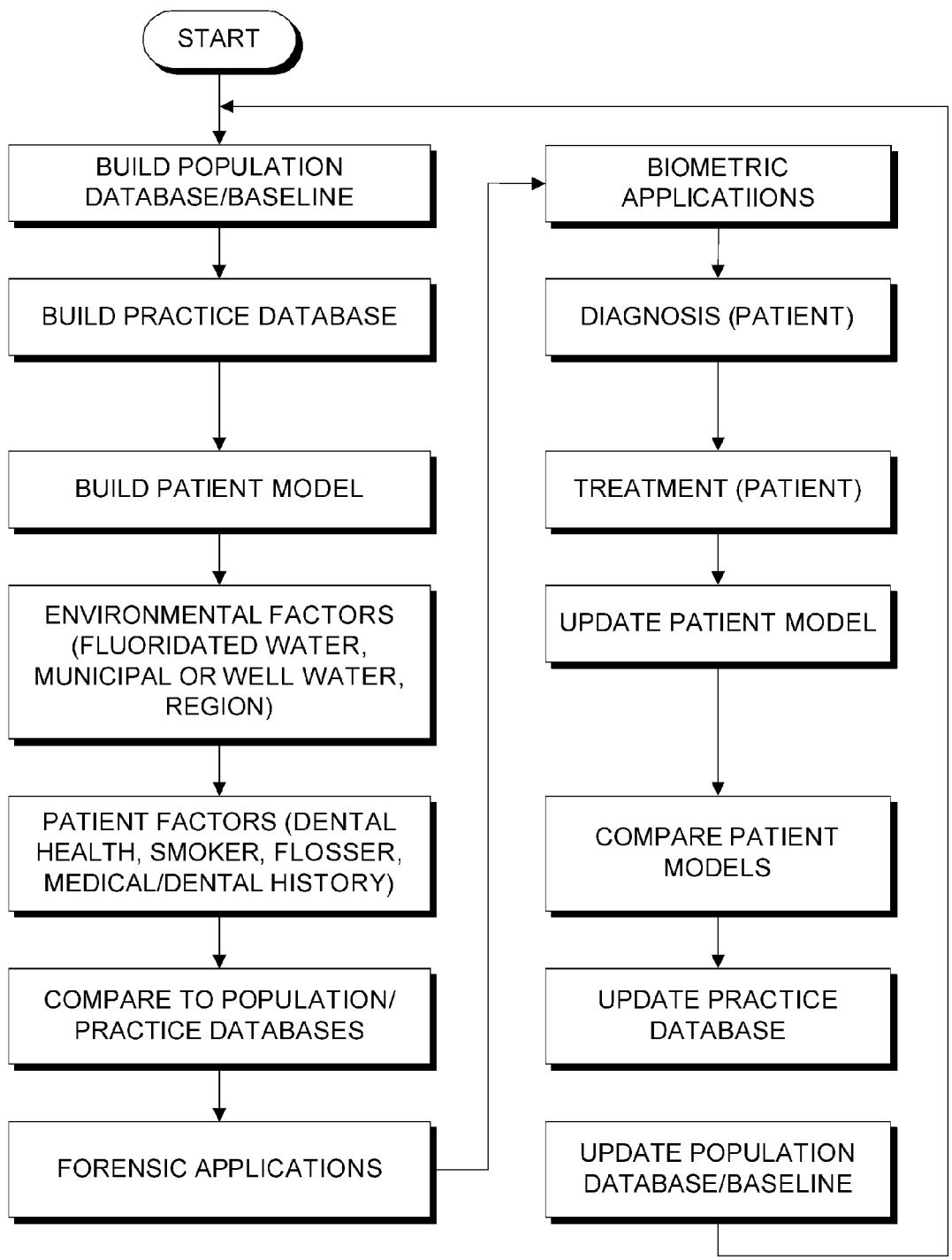
FIG. 7 is a flowchart of a general population baseline database densitometry modeling method according to the present invention.

FIG. 7 shows a flowchart for creating a baseline database, utilizing same in a dental or medical practice, and building individual patient densitometry models. As shown, the process is interactive with individual patient data being utilized in building the practice database, which in turn can be contributed to the general population baseline database. Thus, greater accuracy can be achieved in the baseline database over a period of time with contributed data from individual patients and practices. Still further, the individual patient model can be updated with each visit, and monitored against projected patient densities, as derived from the baseline.

Environmental factors, such as fluoridated, municipal or well water and geographic regional considerations can be applied as shown. Likewise, patient factors can influence the densitometry models. These include general dental health, dental hygiene (such as frequent and thorough brushing and flossing), systemic influences, oncology, zerostomia (dry mouth), transplant patients on anti-rejection medication, susceptibility to infection and decay, etc.

Additional embodiments and aspects of the method of the present invention include a number of additional applications of densitometry modeling, such as forensics, biometrics and individual identification. For example, individual identification from dental and medical records can be expedited by the digital data capture, processing, comparison and display techniques and procedures disclosed herein and adapted for use with densitometry models. In addition to the medical and dental applications, such procedures and the resulting models have applications in such fields as forensics, security (e.g., biometric identification techniques) and law enforcement.

Figure 8D:
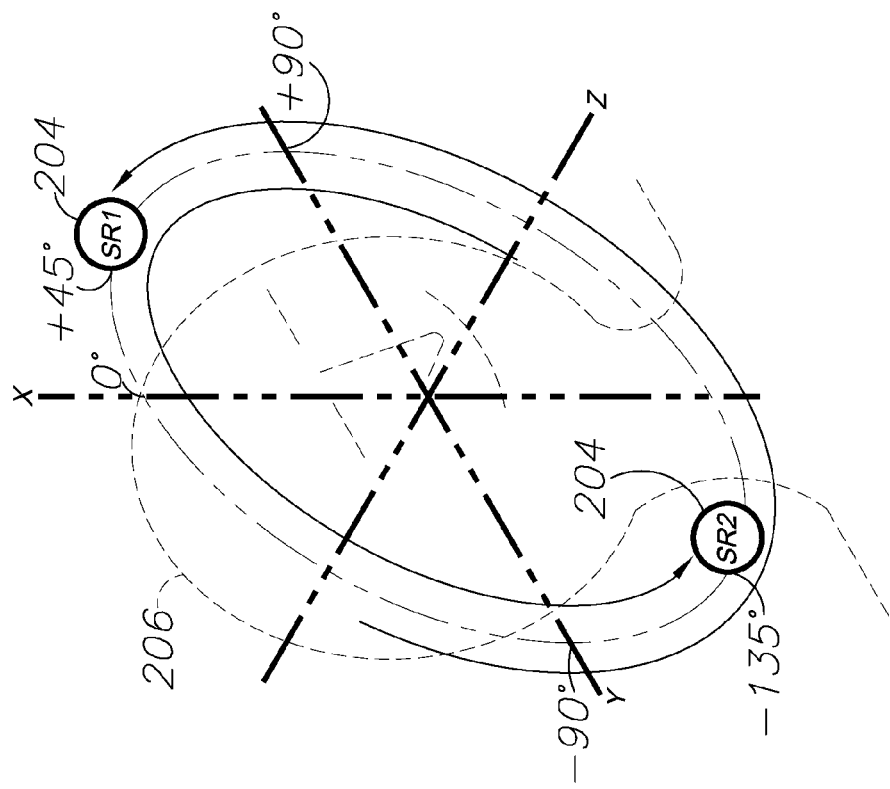
Figure 8C:
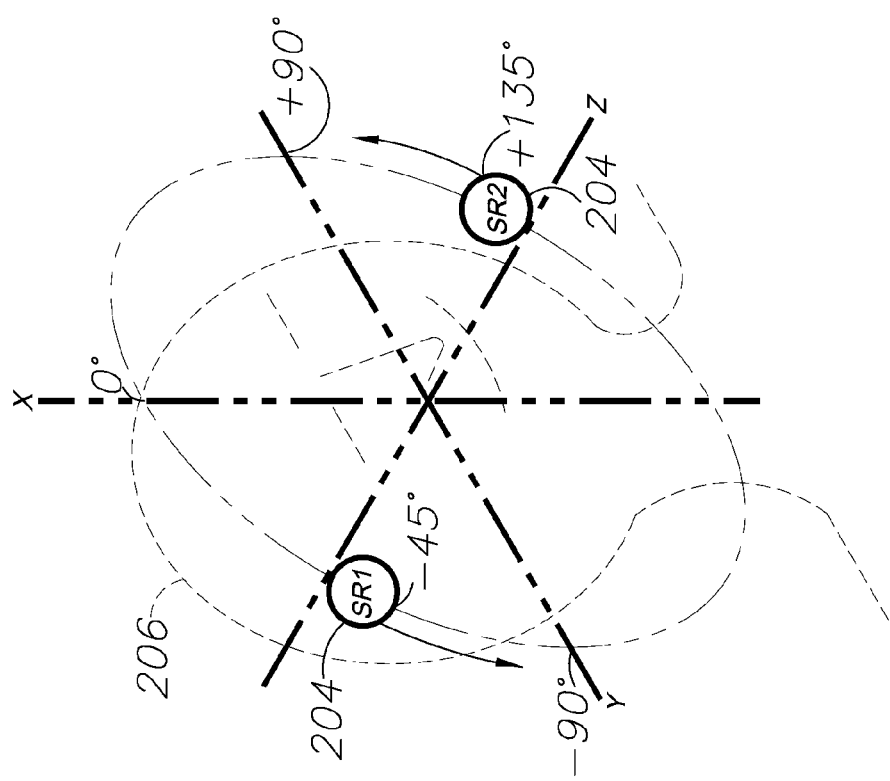

VI. Digital Tomosynthesis Modeling/Imaging Systems, Methods and Applications FIGS. 8A-D show a digital tomosynthesis radiographic densitometry modeling system 202 embodying another aspect of the invention and including a pair of combination source/receptor units 204 (SR1, SR2) each including a radiation source and a radiation receptor or sensor. The system 202 can utilize a variety of suitable modalities for capturing densitometry data. For example, dual energy x-ray absorptiometry (DEXA) uses low and high energy receptor sources and provides advantages for imaging and modeling, which are well-known in the field of dental imaging. The source/receptor units 204 are mounted on a suitable tracking device, which is adapted for revolving them around rotational axes corresponding to the position and orientation of a patient 206 relative to the system 202. As shown in FIGS. 8A-D, axes labeled X, Y and Z are defined relative to the head of a patient. Thus, the source/receptor units 204 rotate in a generally horizontal plane around the X axis (extending top-to-bottom) through approximately 270°. For example, SR1 rotates from a −135° (7:30 relative to a clock face) position (FIG. 8A) to a +135° (4:30 relative to a clock face) position (FIG. 8B) in either a clockwise (as shown) or a counterclockwise direction. The source/receptor units 204 operate to collect continuous densitometry signals using dual-energy techniques and components, which are well-known, whereby a first tomographic slice model is created. For dual energy x-ray absorptiometry (DEXA) modality operation, the source/receptor units 204 make two passes, each at a respective high/low energy level. A second planar tomographic slice model is created by rotating the source/receptor units 204 clockwise around the Z axis (extending anterior-to-posterior). For example, SR1 rotates from a −45° (10:30 clock face) starting position (FIG. 8C) clockwise to a +45° (1:30 clock face) ending position (FIG. 8D). Tomographic information can also be obtained by rotating the source/receptor units 204 around the Y axis (extending from side-to-side).

The resulting tomographic data are integrated and a 3-D image or model is calculated using this information. The extrapolation procedure includes the step of correcting and filtering the collected data in order to eliminate errors and distortion for a much higher degree of accuracy and comprehensiveness than would otherwise be possible with, for example, 2D computer modeling techniques. It will be appreciated that the tomographic slicing planes can be rotated or shifted axially as appropriate for modeling the region of interest (ROI). For example, the modeling procedure can be focused by locating the rotational centers of the source/receptor units 204 approximately on regions of interest (ROIs), with the entire 3-D digital tomosynthesis model being approximately centered thereon.

The applications of the modified system 202 include monitoring osseointegration of prostheses (i.e. orthopedic and dental) for diagnosing the effectiveness of prosthetic implant procedures and detecting potential problems and failures. Load-bearing prostheses can be regularly monitored for problems associated with loading whereby effective measures can be taken in a timely manner. Related problems can arise if the osseo-prosthesis interface should become septic, which can lead to inflammation. In addition to radiographic sensing and modeling, thermographic data can be collected at specific areas of interest, such as prosthesis-tissue interfaces, and used to create graphic models which are useful for diagnosing and treating inflamed tissue conditions associated with septic conditions and other conditions causing inflammation, scarring and necrosis. The system 202 is also useful for 3-D morphology modeling of pulpal chambers and canals for endodontic applications.

Figure 9B:
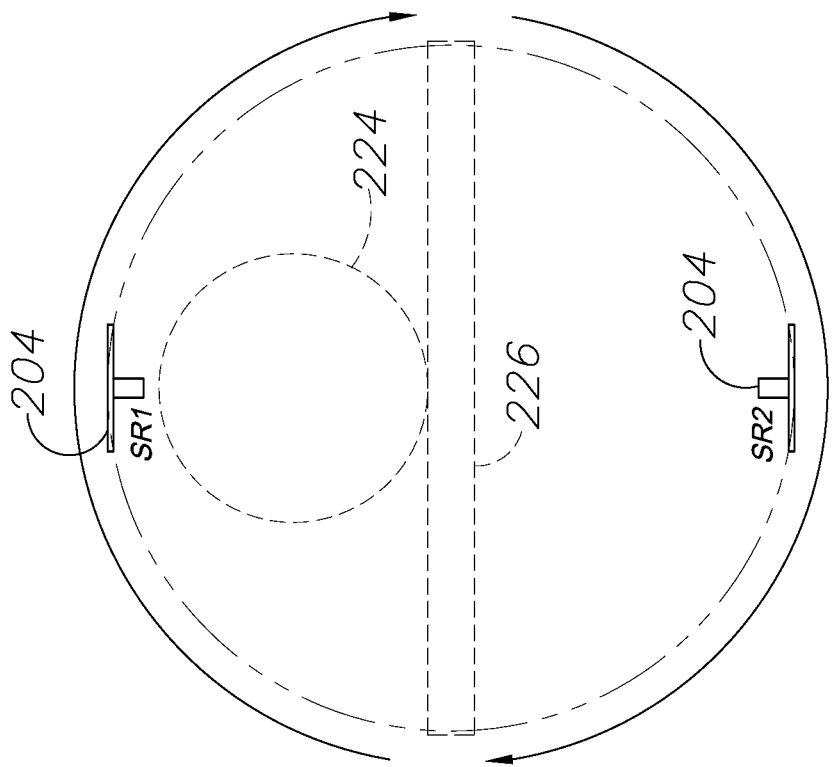
FIGS. 9A-B show another alternative embodiment of the invention comprising another pair of sensor/source units adapted for rotating around a patient or a patient body part.
Figure 9A:
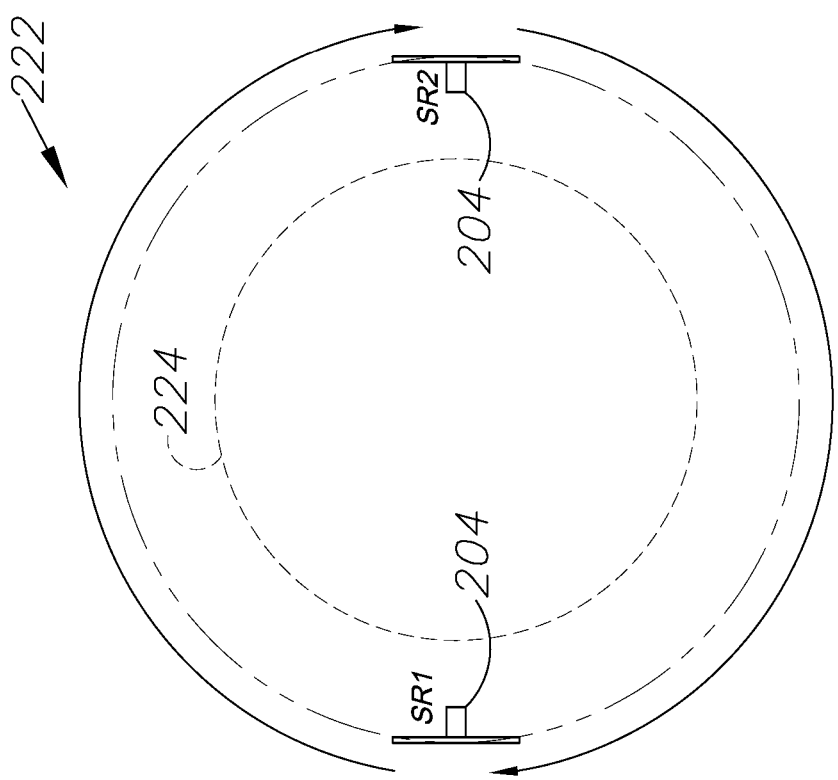

FIGS. 9A,B show another system 222 including source/receptor units 204 (SR1, SR2) mounted on suitable equipment for rotating through approximately 180° around a patient 224, e.g., a head, torso, limb, extremity, etc. As shown in FIG. 9B, a supporting structure 226, such as a table, can be provided for supporting the patient and the rotational apparatus in fixed relation.

FIGS. 10-12 show an application for digital tomosynthesis involving a hip prosthesis 232, which forms an area of osseointegration 234 with the femur 236. A path to be scanned 238 is defined along the length of the embedded shaft portion 240. Any of the various digital tomosynthesis techniques can be utilized for constructing the 3-D radiographic densitometry model, including those performed with the equipment and systems discussed above. FIG. 11 shows the resulting image from a filtering technique, which eliminates the signals corresponding to the osteal cement at the femur-prosthesis interface, and displays the femur bone structure only. FIG. 12 shows the reverse, with the osteal cement displayed in the resulting 3-D model. Such filtering techniques are well-known and can effectively eliminate scatter associated with fragments of bone, etc. Moreover, by controlling the filtering process various conditions can be detected, monitored, diagnosed and treated. For example, hairline fractures can be more easily detected using tomographic densitometry models than conventional x-rays.

Figure 14:
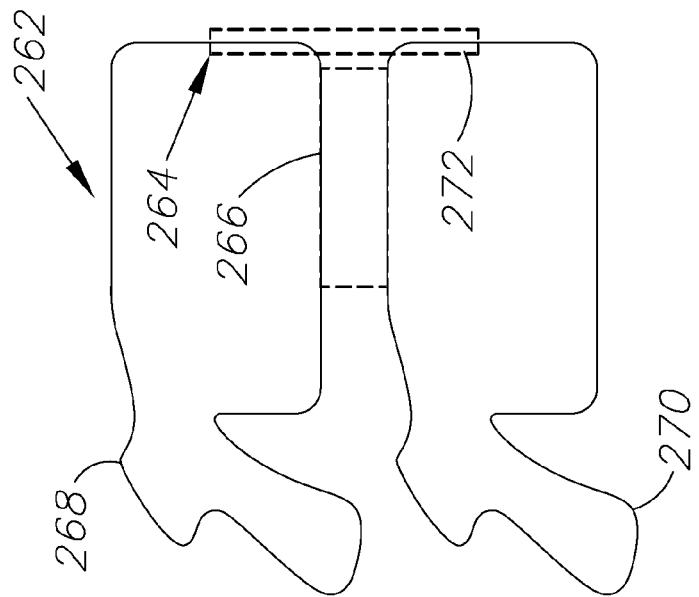
FIG. 14 shows an application of the invention in connection with invertebral fusion cages and plates.
Figure 13:
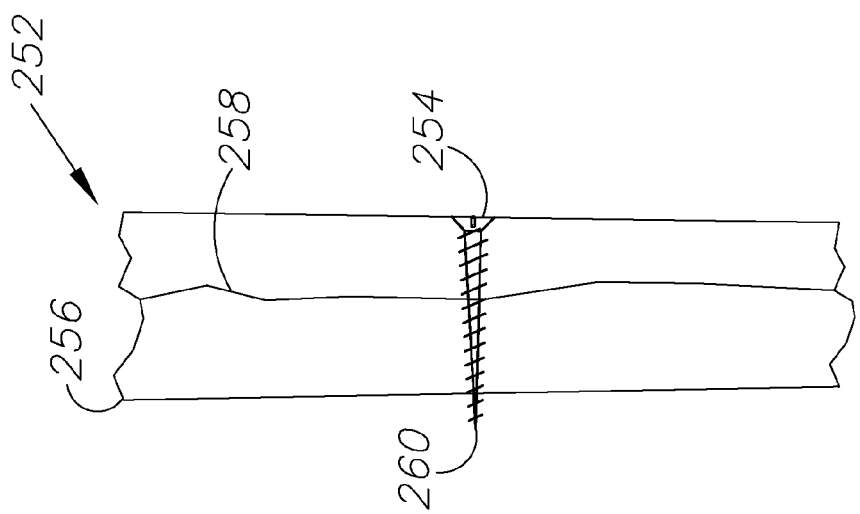
FIG. 13 shows an application of the invention in connection with detecting a bone screw protrusion.

FIG. 13 shows another application 252 involving a bone screw 254 extending through a bone 256 for closing a fracture 258. A tip 260 of the screw 254 protrudes from the surface of the bone 256, and could impede healing if not corrected. FIG. 14 shows another application 262 of the invention in connection with a spinal prosthesis, e.g. a vertebral cage structure 264 including a prosthetic disk portion 266 located between vertebrae 268, 270 and a vertebra-connecting plate 272. The present invention has utility in connection with spinal procedures whereby osseointegration, patient-prosthesis interfaces and various pathologies can be closely monitored. Close monitoring can be particularly important in spinal procedures because of the load-bearing conditions involved, and the significant effects on patient functionalities which are directly affected by such procedures and follow-up therapeutic and rehabilitation treatment.

Figure 15:
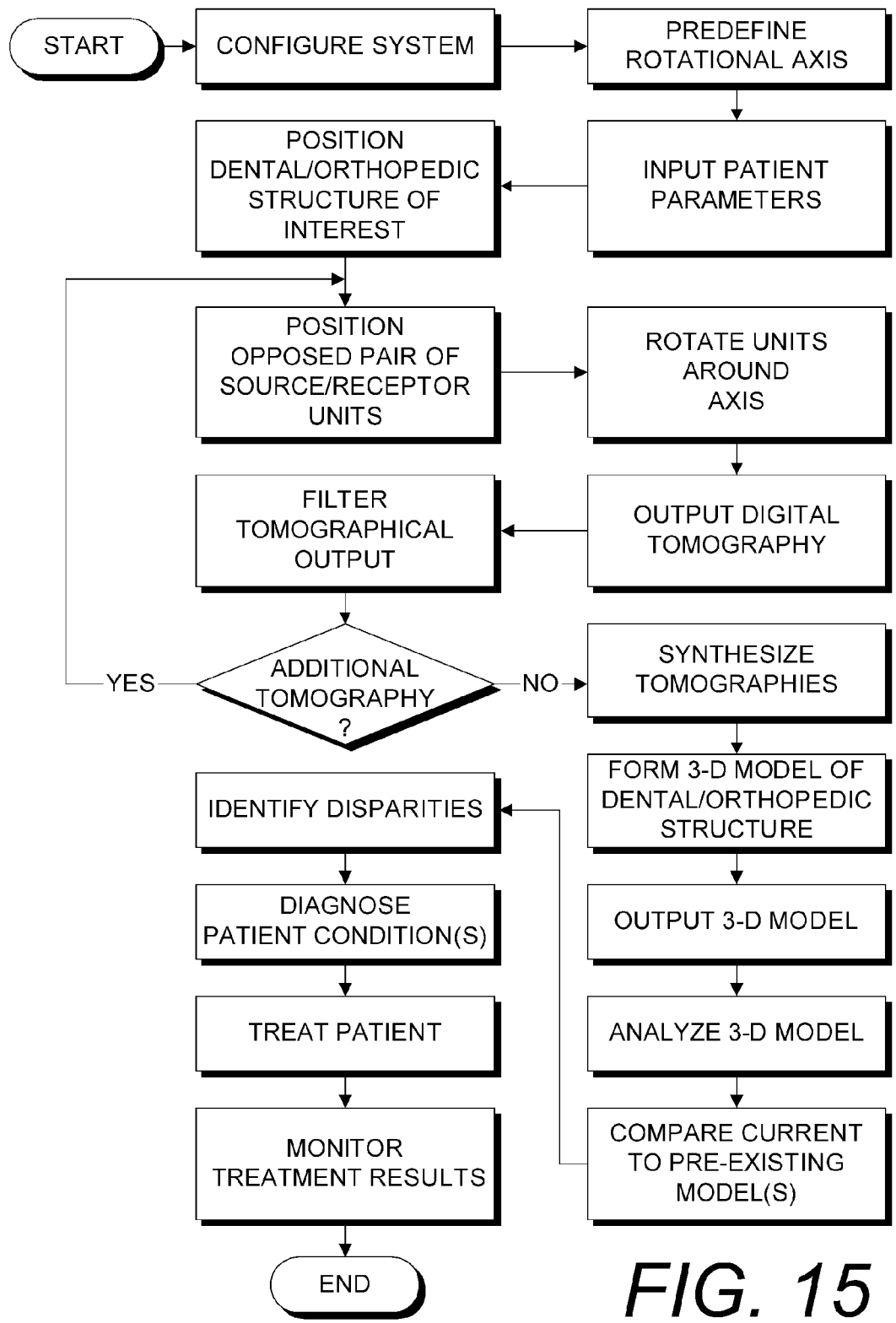
FIG. 15 is a flowchart for a digital tomosynthesis radiographic densitometry modeling method according to the present intention.

A flowchart of a method embodying an aspect of the present invention is shown in FIG. 15 and begins with configuring the system, e.g. preprogramming the controller according to various patient-specific parameters and other operating conditions, such as the rotational axes or paths of the source/receptor units 204. The patient region of interest (ROI) is positioned relative to the system. As described above, such patient positioning generally involves placing the patient ROI between a pair of source/receptor units 204. The system is programmed for rotating the units 204 around a first axis, and can also move the source/receptor units 204 axially, with radiographic densitometry information being output and filtered as necessary. In a DEXA operating mode, two passes (either rotary or axial) are made for each axis, one each at low and high energy levels in order to capture complete densitometry data corresponding to the different tissue types (i.e. hard and soft tissues). Rotation around a second axis, and optionally around a third axis, can provide output in the form of additional radiographic densitometry information necessary to form a 3-D model by computer integration of the resulting signals, e.g., through a process such as digital tomosynthesis. The 3-D model can be output to a monitor, printer or other device, including a computer network or the Internet (worldwide web). The current 3-D model can optionally be compared to pre-existing models in order to detect changed conditions, which can be representative of either improving or worsening conditions. For example, disparities between such models formed at different times can indicate such changed conditions and can facilitate diagnosis. Treatment steps can next be implemented as appropriate and can be guided by the results of such modeling, analysis, comparison and diagnosis steps.

Figure 16:
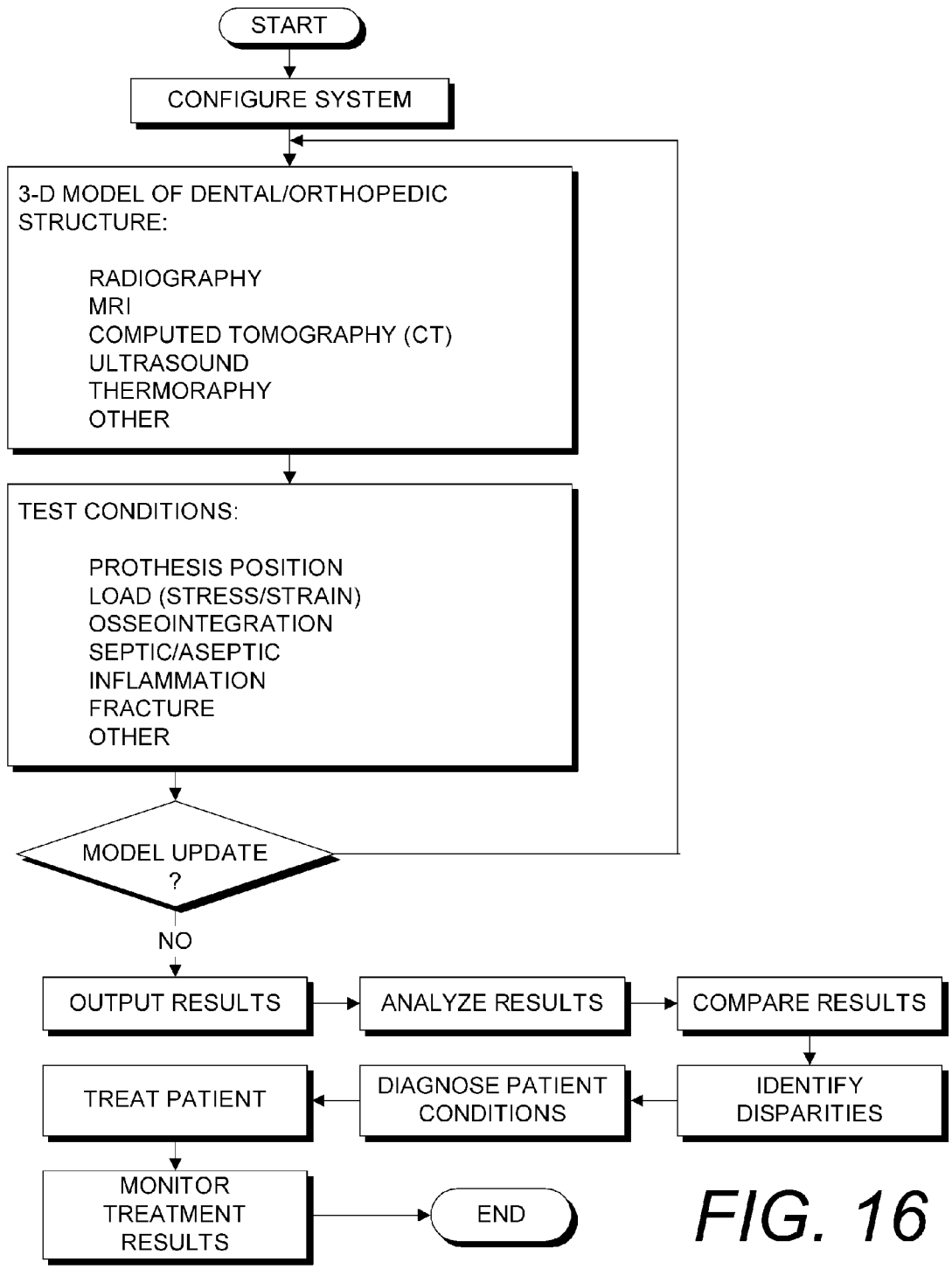
FIG. 16 is a flowchart for another medical/dental imaging/modeling method according to the present invention.

FIG. 16 shows another flowchart with an indication of the range of alternative steps and information sources applicable to the imaging and modeling methods disclosed herein. For example, the imaging technologies currently available include radiography, MRI, computed tomography (CT), ultrasound, fluoroscopy, sonar, Doppler effect, photon emission tomography (PET), single photon emission computed tomography (SPECT) scan and thermography. A variety of conditions can be tested for, including prosthesis position, load (i.e. stress and strain on the prosthesis or surrounding ROI), osseointegration, septic/aseptic conditions, inflammation, morphologies (e.g., pulpal chambers and canals for endodontics) in dentistry and fractures. The method shown in the flowchart of FIG. 16 can otherwise be similar to the methods discussed above.

VII. Osseo Classification System and Method

Figure 17:
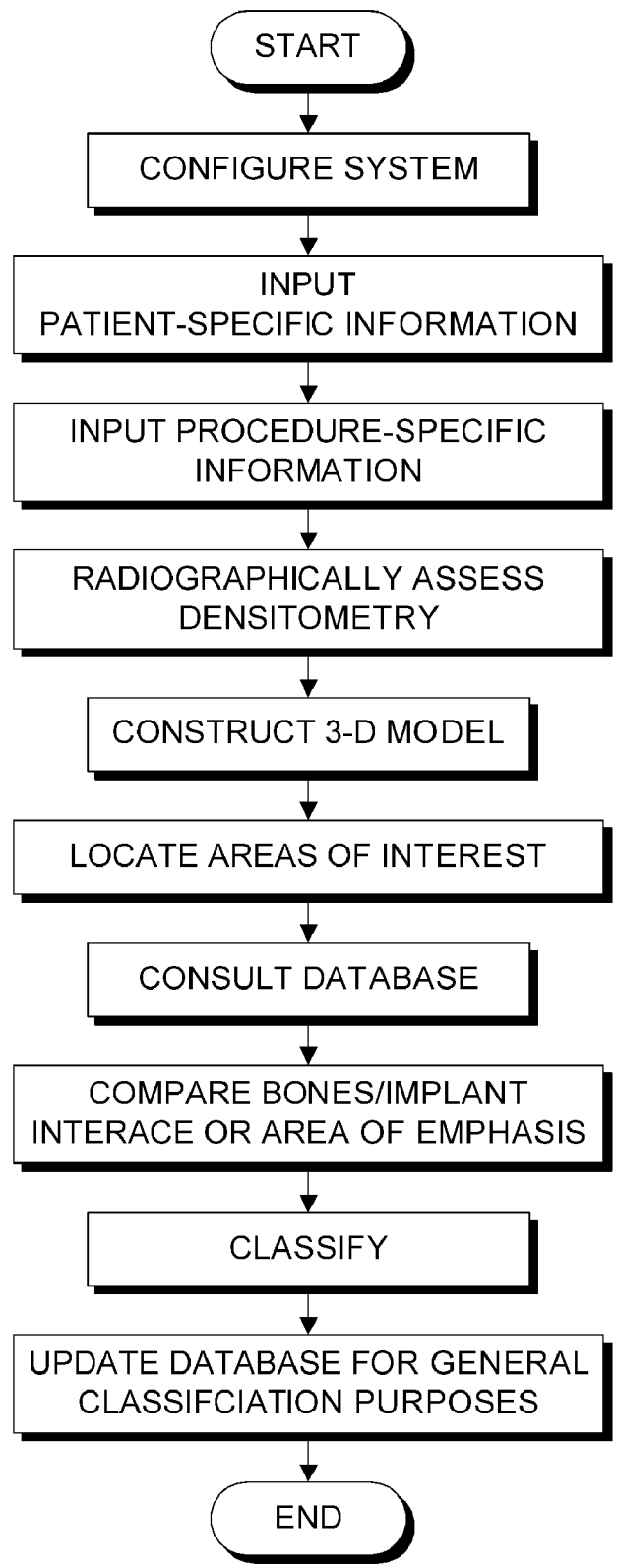
FIG. 17 is a flowchart for another medical/dental imaging/modeling method according to the present invention, e.g., for classifying bone density prior to a procedure.

FIG. 17 shows an osseo classification method embodying another aspect of the present invention, which can be practiced with the systems described above. From a start condition the system is configured, e.g., software is selected and loaded and parameters are input. Such parameters can include, without limitation, patient-specific information such as age, gender, medical history, physical condition and vital signs. Other input parameters can include procedure-specific information pertaining to procedural steps and results, including diagnostic assessments, testing protocols and follow-up treatments.

Densitometry can next be radiographically assessed using equipment and procedures such as those discussed above. Densitometry information is then used to construct a 3-D model, on which areas of interest are located. For example, potential sites for prosthetic implants can be located and analyzed for probable outcomes of an implant procedure. A database can be constructed and/or consulted in connection with this step for deriving additional information pertaining to prosthetic implants and other procedures, such as demographical and other information suited for storage in a database. As discussed above, measured bone density (g/cm$^3$), Z-score (standard deviations above or below the mean for the patient's age and gender) and T-score (standard deviations above or below the mean for a healthy 30-year-old adult of the same gender) are commonly used for diagnosing osteoporosis and susceptibility to fractures. Such patient-specific data can be obtained and calculated using the systems and methods of the present invention by radiographically measuring densitometry and by accessing the appropriate databases with corresponding data for a population sample. A variety of useful models and projections can be obtained, including useful information for planning treatment procedures and for determining the probabilities of successful outcomes with various prostheses. Osseo classification according to the four types discussed above can also be accomplished using the systems and methods of the present invention, and prosthetic implant procedures planned accordingly.

Information retrieved from a database can be compared to the actual bone/implant interfaces or areas of interest, which were input during the patient-specific and procedure-specific input steps. Based on the results of such comparisons, the osseo structures at the regions of interest are classified. The database can then be updated for general classification purposes, and the preclassification phase ends.

Normally the preclassification procedure discussed above leads to a treatment procedure, such as implanting a prosthesis. It will be appreciated that preclassifying the osseo structure and assigning the appropriate classification types to the areas of interest can guide the healthcare practitioner in performing the most appropriate and beneficial treatment(s). For example, the bone density types normally relate directly to suitability for implanting prosthetics at particular prospective implant sites. Of course, prospective implant sites can be ruled out based on unacceptable bone densitrometry findings, e.g., Type 4, which is generally unsuitable for many types of prosthetic devices. Such information can also be utilized to determine prognoses for implant procedures, especially those relying on structural (e.g., load-bearing) osseo-integration for restoring patient functions.

It is to be understood that while certain aspects and embodiments of the invention are described and shown, the invention is not limited thereto and can assume a wide range of other, alternative aspects and embodiments.

What is claimed and desired to be secured by Letters Patent is as follows:

1. A method of classifying osseo structure and/or prosthetic osseointegration using 3-D digital tomosynthesis medical and dental modeling, which comprises the steps of:
    providing a computer including a digital memory adapted for storing patient densitometry information, an input and an output;
    providing an input subsystem including a pair of source/receptor units each including a signal source and a receptor;
    providing said input subsystem with a DEXA modality;
    providing said signal positioning subsystem with a rotating mechanism mounting said source/receptor units in generally opposite relation with a patient region of interest (ROI) located therebetween;
    rotating said source/receptor units in both directions through coplanar, circular paths of movement around a first rotational axis;
    providing a signal positioning subsystem connected to said computer and mounting said source and receptor, said positioning subsystem moving said source and/or said receptor through a predetermined path of movement relative to a patient;
    rotating said source/receptor units in a first direction with said input subsystem at a low energy level and rotating said source/receptor units in a second direction with said input subsystem at a high energy level;
    providing said signal positioning subsystem with a second rotational axis defining a second set of coplanar, circular paths of movement of said source/receptor units;
    corresponding said first rotational axis to an X axis extending top-to-bottom relative to the patient;
    corresponding said second rotational axis to a Z axis extending front-to-back relative to the patient;
    providing said circular paths of movement with ranges of approximately between 90° and 270°;
    connecting said receptor to the computer input;
    producing signals with said receptor to said computer input representing a condition of the patient's dental and/or orthopedic structure;
    integrating signals obtained along said first and second paths of movement;
    modeling a patient ROI in three dimensions from said integrated signals;
    filtering tomographic information from said receptors;
    subtracting signals corresponding to scatter and other extraneous information and reversing the polarity and output of signals representing different types of structure;
    constructing multiple slices at different depths and with different thicknesses from individual tomographic data acquisitions;
    creating, storing and comparing 3-D digital models of patient dental and/or orthopedic structure;
    providing an output device connected to said computer output and adapted for communicating patient condition information consisting of or derived from a respective said 3-D digital model;
    providing a database accessible by said computer and including information chosen from among the group consisting of patient history, age, gender and locations;
    assessing and modeling patient parameters chosen from among the group consisting of:
    prosthesis position, load (stress/strain), osseointegration, septic/aseptic, inflammation and fracture; and
    classifying osseo structure and/or prosthetic osseointegration based on said densitometry data.

* * * * *